United States Patent [19]

Eggler et al.

[11] 4,268,522

[45] May 19, 1981

[54] 13,14-DIHYDRO-15-ALKENYL- AND 13,14-DIHYDRO-15-ALKYNYL PROSTAGLANDINS AND ANALOGS THEREOF

[75] Inventors: James F. Eggler, Stonington; Hans-Jurgen E. Hess, Old Lyme, both of Conn.

[73] Assignee: Pfizer Inc., New York, N.Y.

[21] Appl. No.: 85,907

[22] Filed: Oct. 18, 1979

Related U.S. Application Data

[62] Division of Ser. No. 695,420, Jun. 14, 1976, abandoned.

[51] Int. Cl.$^3$ .............................................. G07C 171/00
[52] U.S. Cl. .............................. 424/305; 260/843.3 P; 260/845.7 P; 260/846.22; 560/53; 560/121; 562/463; 562/503; 424/317

[58] Field of Search .................. 560/121; 562/503; 424/305, 317

[56] References Cited

U.S. PATENT DOCUMENTS 4,073,934  2/1978  Skuballa et al. ............... 424/305

Primary Examiner—Robert Gerstl
Attorney, Agent, or Firm—Connolly and Hutz

[57] ABSTRACT

The invention discloses certain novel 13,14-dihydro-15-alkenyl prostaglandins and 13,14-dihydro-15-alkynyl prostaglandins and analogs of each as well as the novel intermediates employed in their preparation. The 9-oxo compounds of this novel series demonstrate selective bronchodilator activity, certain of these are also useful as antisecretory agents.

5 Claims, No Drawings

13,14-DIHYDRO-15-ALKENYL- AND 13,14-DIHYDRO-15-ALKYNYL PROSTAGLANDINS AND ANALOGS THEREOF

CROSS REFERENCE TO RELATED APPLICATION

This application is a division of application Ser. No. 695,420, filed June 14, 1976 and now abandoned.

BACKGROUND OF THE INVENTION

1. Field of the Invention

The invention relates to a novel series of 13,14-dihydro-15-alkenyl prostaglandins and 13,14-dihydro-15-alkynyl prostaglandins, certain analogs, esters thereof and novel intermediates for their preparation. In particular, it relates to novel 9-oxo-11α,15-dihydroxyprosta-5,16-dienoic acids, 9-oxo-11α,15-dihydroxyprosta-5-ene-16-yneoic acids, certain analogs and esters thereof which possess selective bronchodilator activity; and various novel intermediates useful in their preparation. The 17-phenyl-ω-trinorprostaglandins of this series also possess useful antisecretory activity.

2. Description of the Prior Art

The prostaglandins are C-20 unsaturated fatty acids which exhibit diverse physiological effects. Each of the known naturally occurring prostaglandins is derived from prostanoic acid which has the structure and position numbering:

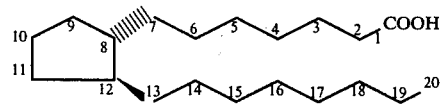

[Bergstrom et al., Pharmacol. Rev., 20, 1 (1968), and references cited therein] A systematic name for prostanoic acid is 7-[(2β-octyl)-cyclopent-1α-yl]heptanoic acid.

$PGE_2$ has the structure:

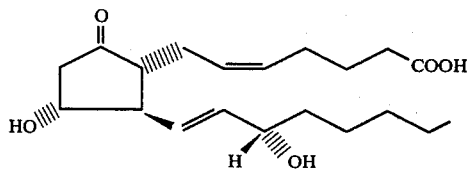

$PGF_{2\alpha}$ has the structure:

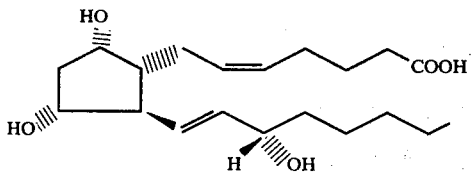

$PGF_{2\beta}$ has the structure

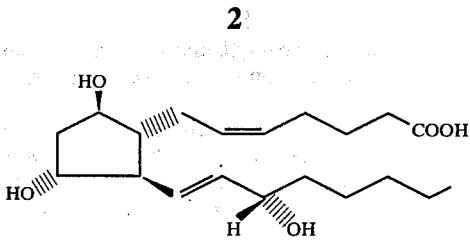

$PGA_2$ is 11-desoxy-$PGE_2$ with a double bond in the 5-membered ring between carbons 10 and 11.

$PGB_2$ is identical to $PGA_2$, except that the double bond is shifted to the 8,12-position.

Each of the $PG_1$ prostaglandins, $PGE_1$, $PGF_{1\alpha}$, $PGF_{1\beta}$, $PGA_1$ and $PGB_1$, has a structure the same as the corresponding $PG_2$ compound except that the cis double bond between C-5 and C-6 is replaced by a single bond.

Broken line attachments to the cyclopentane ring indicate substituents in alpha configuration, i.e., below the plane of the cylopentane ring. Solid line attachments to the cyclopentane ring indicate substituents in beta configuration, i.e., above the plane of the cyclopentane ring.

The side-chain hydroxy at C-15 in the above formulas is in S configuration. [See Nature, 212, 38 (1966) for discussion of the stereochemistry of the prostaglandins]

The various physiological effects of the prostaglandins are reviewed in "The Prostaglandins, Progress in Research," Wiley-Interscience Division of John Wiley and Sons, Inc., New York, N.Y., 1972, M. M. Karim, editor. For instance, the prostaglandins of the E and A series are potent vasidilators (Bergstrom, et al., Acta. Physiol. Scand., 64: 332-33, 1965 and Bergstrom, et al., Life Sci., 6: 449-455, 1967) and lower systemic arterial blood pressure (vasodepression) on intravenous administration (Weeks and King, Federation Proc. 23: 327, 1964; Bergstrom, et al., 1965, op. cit.; Carlson, et al., Acta. Med. Scand., 183: 423-430, 1968; and Carlson, et al., Acta. Physiol. Scand., 75: 161-169, 1969). Another well known physiological action for $PGE_1$ and $PGE_2$ is as a bronchodilator (Cuthbert, Brit. Med. J., 4: 723-726, 1969).

Another important physiological role for the natural prostaglandins is in connection with the reproductive cycle. $PGE_2$ is known to possess the ability to induce labor (Karim, et al., J. Obstet. Gynaec. Brit. Cwlth., 77: 200-210, 1970) and also to induce therapeutic abortion (Bygdeman, et al., Contraception, 4: 293, 1971) and to be useful for control of fertility (Karim, Contraception, 3: 1973, 1971). Patents have been obtained for several prostaglandins of the E and F series as inducers of labor in mammals (Belgian Pat. No. 754,158 and West German Pat. No. 2,034,641), and on $PGF_1$, $F_2$, and $F_3$ for control of the reproductive cycle (South African Pat. No. 69/6089).

Still other known physiological activities for $PGE_1$ are in the inhibition of gastric acid secretion (Shaw and Ramwell, in: Worcester Symp. on Prostaglandins, New York, Wiley, 1968, pages 55-64) and also of platelet aggregation (Emmons, et al., Brit. Med. J., 2: 468-472, 1967).

Very small doses of $PGE_1$ and $PGE_2$ have been found to cause diarrhea in animals including humans (Bennett, in The Prostaglandins, Progress in Research, Wiley-Interscience Division of John Wiley and Sons, Inc., New York, N.Y., 1972, M. M. Karim, editor, pages 212-214).

Use of the natural prostaglandins as bronchodilators is complicated by the above-mentioned diversity of activity.

The synthesis of the novel compounds of the invention employs 2-[5α-hydroxy-3α-(tetrahydropyran-2-yloxy)-2β-aldehydocyclopent-1α-yl]acetic acid, γ-lactone [Corey, et al., *J. Amer. Chem. Soc.*, 93, 1490 (1971)] as starting material.

SUMMARY OF THE INVENTION

The novel compounds of the invention are those of the formula (I)

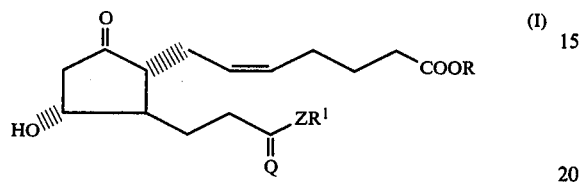

(I)

wherein R is hydrogen or biphenyl; $R^1$ is a member selected from the group consisting of hydrogen, phenyl and alkyl having from one to eleven carbon atoms; Q is a member selected from the group consisting of oxygen,

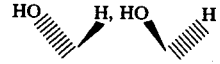

and mixtures of

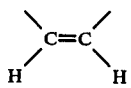

and Z is a member selected from the group consisting of —C≡C,

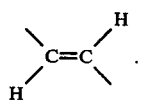

and

The compounds of formula (I) are potent bronchodilators with greater selectivity than the natural prostaglandins. Especially valuable as selective bronchodilators are the compounds of formula (I) wherein Q is said mixture of

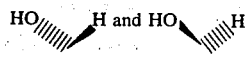

and $R^1$ is n-$C_3H_7$ or n-$C_5H_{11}$. Compounds of formula (I) wherein $R^1$ is phenyl are also valuable as antisecretory agents.

It is further object of the invention to provide the following novel intermediates for the preparation of compounds of formula (I):

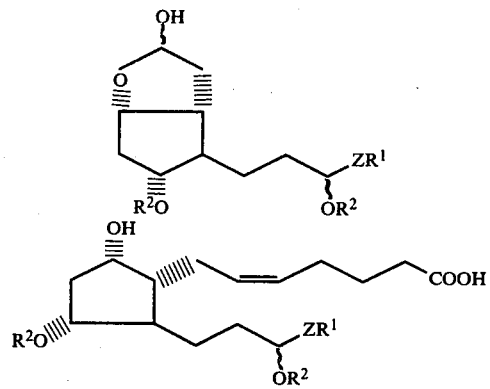

wherein $R^2$ is 2-tetrahydropyranyl and Z and $R^1$ are as previously defined.

DETAILED DESCRIPTION OF THE INVENTION

The synthesis of the compounds of formula (I) wherein Z is —C≡C— and

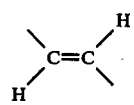

is depicted in Scheme A, below. Within the context of this invention, when the letters a, b, c are used after the Roman numerals which identify the various structures, said letters indicate the following;

a, Z is —C≡C— b, Z is 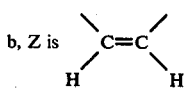

c, Z is 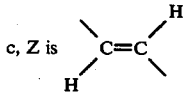

Scheme A

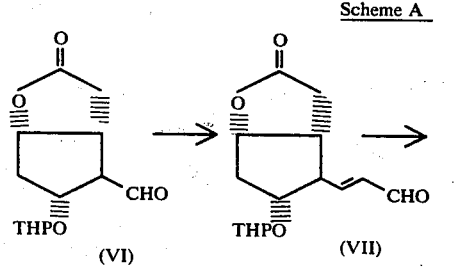

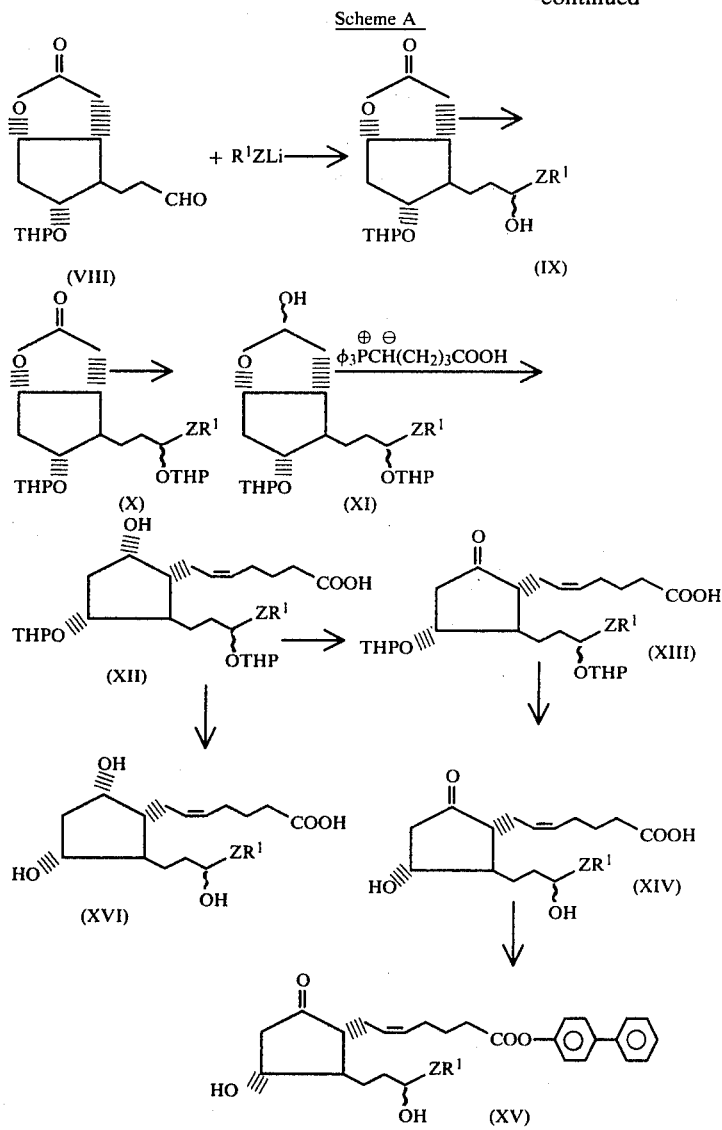

The waved line attachment ( ) used herein indicates a mixture of the two possible configurations.

$\phi = C_6H_5$; THP = 2-tetrahydropyranyl.

(IXa) through (XVIa): Z is —C≡C—

(IXb) through (XVIb): Z is

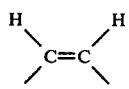

(IXc) through (XVIc): Z is

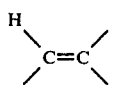

For the first step in the preparation of the compounds of formula (I), the starting material of formula (VI), 2-[5α-hydroxy-3α-(tetrahydropyran-2-yloxy)-2β-aldehydocyclopent-1α-yl]acetic acid, γ-lactone, [Corey et al., Journ. Amer. Chem. Soc. 93, 1490 (1971)] is reacted with formylmethylene dimethylphenylphosphonium ylide to obtain the intermediate 2-[5α-hydroxy-3α-(tetrahydropyran-2-yloxy)-2β-(2-formylvinyl)cyclopent-1α-yl]acetic acid, γ-lactone (VII). This step is carried out in the presence of a reaction inert organic solvent under anhydrous conditions. Examples of such solvents are methylene chloride, chloroform, ethyl ether, tetrahydrofuran, toluene, hexane and the like. The compound of formula (VI) and said ylide are employed in approximately equimolar amounts. The reaction is preferably carried out at a temperature in the range of about −50° to 30° (all temperatures herein are given in degrees Centigrade) and in an inert atmosphere for periods of from about 2 hours to 2 days. The desired product of formula (VII) is isolated and purified by standard methods known in the art. The formylmethylene dimethylphosphonium ylide used in the above reactions is prepared by addition of a molar excess of a lower alkyl formate ester such as etyl formate to the lithium salt which results when approximately equimolar amounts of phenyltrimethylphosphonium bromide and an alkyl lithium such as butyl lithium are comnbined in the presence of a reaction inert organic solvent at about 0°. The ylide is isolated by pouring the reaction mixture onto cold aqueous acid such as dilute hydrochloric acid and extracting with a water immiscible solvent such as ethyl ether or methylene dichloride. The aqueous layer is then basified and extracted. After evaporation of the washed and dried extracts the residual ylide is obtained. Since the ylide is unstable it is preferably used without delay in the above reaction.

In the second step, the intermediate of formula (VII) obtained above is contacted with hydrogen to provide the valuable intermediate of formula (VIII), 2-[5α-hydroxy-3α-(tetrahydropyran-2-yloxy)-2β-(2-formylethyl)cyclopent-1α-yl]acetic acid, γ-lactone. The hydrogenation is carried out in the presence of a catalytic amount of a metal catalyst under conditions known to selectively reduce olefinic double bonds without reducing the aldehyde moiety, see for example, Freifelder, "Practical Catalytic Hydrogenation", Wiley Interscience Division of John Wiley and Sons, Inc., New York, N.Y., 1971, pp. 150–154.

In accordance with the process for preparing the compounds of the invention, the α,β-unsaturated aldehyde (VII) is placed in any of a variety of reaction inert solvent mediums in the presence of said catalyst and contacted with hydrogen at an appropriate temperature and pressure until the double bond is reduced. Thereafter, the desired aldehyde (VIII) may be recovered by conventional procedures involving catalyst removal and recovery of the product from the solvent medium.

As used herein "reaction inert solvent medium" refers to any medium which is a solvent or suitable suspending agent for the reactant, is stable under the hydrogenation conditions and does not interfere with the effectiveness of the catalyst or interact with the reactant or product. Polar organic solvents are generally suitable and include the lower alkanols such as methanol, ethanol, and butanol, etc., cyclic and straight chain water soluble ethers such as dioxane, tetrahydrofuran, diethylene glycol monomethylether, and 2-ethoxyethanol.

As will be appreciated, these solvents and others are conventional in known hydrogenation techniques and hence are not critical.

The preferred temperature range for the hydrogenaton is from about 0° to about 60°. Room temperature is especially preferred for reasons of convenience. At temperatures below 0° the reaction is inordinately slow whereas at temperatures about 60°, undesireable by-products may be formed. As is to be expected, the higher the temperature, the faster the reaction rate.

While a wide variety of catalysts known in the art may be employed for this hydrogenation, the preferred catalysts are Raney nickel and the noble metals platinum and palladium. The noble metal catalysts may be either of the supported or non-supported type, as well as the known catalytic compounds thereof such as the oxides, chlorides, etc. Examples of suitable catalyst supports include carbon, silica and barium sulfate. The catalysts may be performed or formed in situ by prereduction of an appropriate salt of the catalytic compound. Examples of preferred catalysts are 5% palladium-on-carbon, 5% platinum-on-carbon, platinum chloride, palladium chloride and platinum oxide. Materials such as the latter, where the metal is in a combined, non-elemental form, generally require prereduction before the hydrogenation can take place. This is accomplished simply by suspending the catalyst precursor in the hydrogenation medium, hydrogenating it, adding the substrate and continuing the hydrogenation. Alternatively, all of the components can be incorporated at once and hydrogenation commenced. The former procedure has the advantage of permitting the operator to separately determine the quantity of hydrogen absorbed during the catalyst prereduction and hydrogenation phase. The extent of hydrogenation can then be more readily controlled. For reasons of efficiency, an especially preferred catalyst is 5% palladium-on-carbon.

The expression "catalytic amount" as used herein is well understood by those skilled in the art of hydrogenation.

The pressure employed during hydrogenation is not critical and pressures of from atmospheric to 2000 p.s.i. are preferred. The hydrogenation is usually completed in a time period which may vary from a few minutes to a few hours.

The intermediate (VIII) is then reacted in the next step with a lithium acetylide of the formula $R^1C\equiv C^\ominus\text{-}Li^\oplus$, a trans-1-alkenyl lithium, of the formula

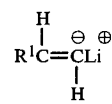

or vinyl lithium to provide novel compounds of formula (IX). When the lithium acetylides are employed, the products of the reaction are of the formula (IXa) in which Z is —C≡C— (ethynylene); when the above mentioned trans-alkenyl lithiums are employed, the products are of the formula (IXc) in which Z is

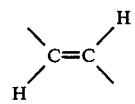

(trans-vinylene); and when vinyl lithium is utilized, the product is of formula (IX) in which $ZR^1$ is —CH=CH$_2$.

The intermediate (VIII) and at least an equimolar amount of one of the compounds $R^1ZLi$ are contacted in the presence of a reaction inert organic solvent under anhydrous conditions and in the presence of an inert atmosphere to provide the desired compounds of formula (IX). The reaction may be carried out at a temperature in the range of from about −100° to −20°, and temperatures of from about −80° to −50° are preferred.

Examples of reaction inert solvents which may be employed are ethyl ether, tetrahydrofuran, tetrahydropyran, hexane and pentane. The reaction is usually complete within a matter of a few minutes to a few hours. The desired product, (IX), is isolated by well-known methods such as pouring the reaction mixture onto ice-water, extracting with a water immiscible organic solvent, and removal of solvent by evaporation. The residue may then be purified, if desired, by standard methods such as column chromatography employing solvents of gradually increasing polarity for elution.

The compounds of formula (IX) are then reacted to introduce an hydroxyl protecting group on the side chain hydroxyl moiety. Suitable hydroxyl protecting groups are those which are stable to basic hydrolysis and readily removed by mild acid hydrolysis. Many of such suitable groups for protecting alcohols are known in the art. See for example: C. D. Djerassi, ed., "Steroid Reactions: An Outline for Organic Chemists", Holden- Day, San Francisco, 1963, pp. 1–89; L. F. Fieser, "Reagents for Organic Synthesis", John Wiley and Sons, Inc., New York, 1968; L. F. Fieser, "Reagents for Organic Synthesis", Volume II, Wiley Interscience, New York, 1969. Examples of such suitable hydroxyl protecting groups are 2-tetrahydropyranyl, 2-tetrahydrofuranyl and dimethyl-t-butylsilyl. The preferred protecting group is 2-tetrahydropyranyl which provides the novel intermediates of formula (X).

The introduction of the preferred 2-tetrahydropyranyl hydroxyl protecting group is carried out by methods well known in the art to provide the compounds (X). For example, the hydroxyl-containing compound of formula (IX) is contacted with at least an equimolar amount of 2,3-dihydropyran under substantially anhydrous conditions in the presence of a reaction inert organic solvent such as chloroform, methylene chloride, ethyl ether, tetrahydrofuran and the like, and a catalytic amount of acid such as sulfuric acid, hydrogen chloride, p-toluenesulfonic acid and the like are added. The mixture is maintained at a temperature in the range of about $-20°$ to $50°$ for a time period of about 15 minutes to 4 hours. The desired product is then isolated by standard methods and is ordinarily used in the next reaction step without further purification.

It should be noted that the abbreviation THP as used herein denotes the 2-tetrahydropyranyl moiety.

Of course, in any of the intermediates of formulae (VI) through (XIII) which contain the 2-tetrahydropyranyl hydroxyl protecting group, the THP group used therein could be replaced by any of the other suitable hydroxyl protecting groups mentioned above such as 2-tetrahydrofuranyl, dimethyl-t-butylsilyl and the like, and use of other such hydroxyl protecting groups is considered to be within the scope and purview of the invention.

In the next step in the process of the invention, the hydroxyl protected lactones of formula (X) are converted to the hemiacetals (XI). The lactone is dissolved in a suitable solvent such as toluene and a solution of diisobutylaluminum hydride in hexane is added. After 1 to 2 hours at a temperature below $-60°$, the reaction mixture is quenched, diluted with ether, washed with aqueous sodium potassium tartrate solution, and dried. Evaporation of solvent affords the crude product (XI) which may be purified further, e.g., by column chromatography on silica gel.

Hemiacetal (XI) is combined with the ylide solution produced from (4-carboxy-n-butyl)triphenylphosphonium bromide and sodium methylsulfinylmethide in dimethylsulfoxide. After a reaction period of from about 30 minutes to a few hours at a temperature in the range of about $0°$ to $80°$ and preferably at about $20°$ to $60°$, the reaction mixture is poured onto ice water. The basic solution thus produced is extracted, for example, with ethyl acetate or ether, acidified, further extracted, washed, dried and concentrated. The crude product of formula (XII) may then be purified, for example, by chromatography.

Oxidation of the 9-hydroxy group of the novel compounds of formula (XII) with Jones' reagent [see Jones et al.., Jour. Chem. Soc., 457, 2548, 3019 (1953)] affords the corresponding 9-oxo compounds (XIII). After exposure of the compound of formula (XII) to approximately an equimolar amount of Jones' reagent, typically at about $-10°$ for about 10 minutes, the reaction mixture is poured onto a water immiscible solvent, typically ethyl acetate, washed with water, dried and concentrated to dryness. The product thus obtained is ordinarily of sufficient purity for use in the next step.

The removal of the hydroxy protecting groups such as the 2-tetrahydropyranyl groups by hydrolysis in dilute acid then affords the desired compounds of formula (XIV). Typically, the hydrolysis is brought about by exposure of the compound (XIII) to an excess of aqueous acetic acid at about room temperature and typically at about $27°$ for about 12 to 18 hours under an inert atmosphere. The reaction mixture is then concentrated by evaporation and the residue purified by chromatography on silica gel.

While the compounds of formulae (XIV) and (XV) were found to have comparable biological profiles, the p-biphenylyl esters (XV) are preferred because of their higher degree of crystallinity and their greater ease of handling. The latter compounds are obtained by esterification of the acids of formula (XIV) with a 3 to 10 molar excess of p-phenylphenol in the presence of a reaction inert organic solvent and in the presence of at least an equimolar amount, based on the compound (XIV), of certain condensing agents known in the art to promote formation of ester bonds. Examples of such agents are the carbodiimides such as dicyclohexylcarbodiimide and 1-ethyl-3-(3-dimethylaminopropyl)carbodiimide hydrochloride. The preferred condensing agent is dicyclohexylcarbodiimide for reasons of economy and efficiency.

Examples of suitable reaction inert organic solvents for carrying out the esterification are methylene chloride, chloroform, trichloroethylene and 1,2-dichloroethane. Typically the reaction is carried out in methylene chloride, under anhydrous conditions and under an inert atmosphere. While the esterification may be carried out successfully over a wide range of temperature such as from about $20°$ to $100°$, it is preferred to combine the reactants and solvent at about room temperature, at which temperature the reaction is ordinarily substantially complete in about 1–2 hours or less. The desired p-biphenylyl ester is isolated by evaporation of solvent and purified by chromatography on silica gel.

As mentioned above, the compounds of the invention obtained by the reaction sequence outlined in Scheme A are those of formula (I) wherein Z is ethynylene or trans-vinylene. The process for preparing the compounds of formula (I) wherein Z is cis-vinylene is outlined below in Scheme B.

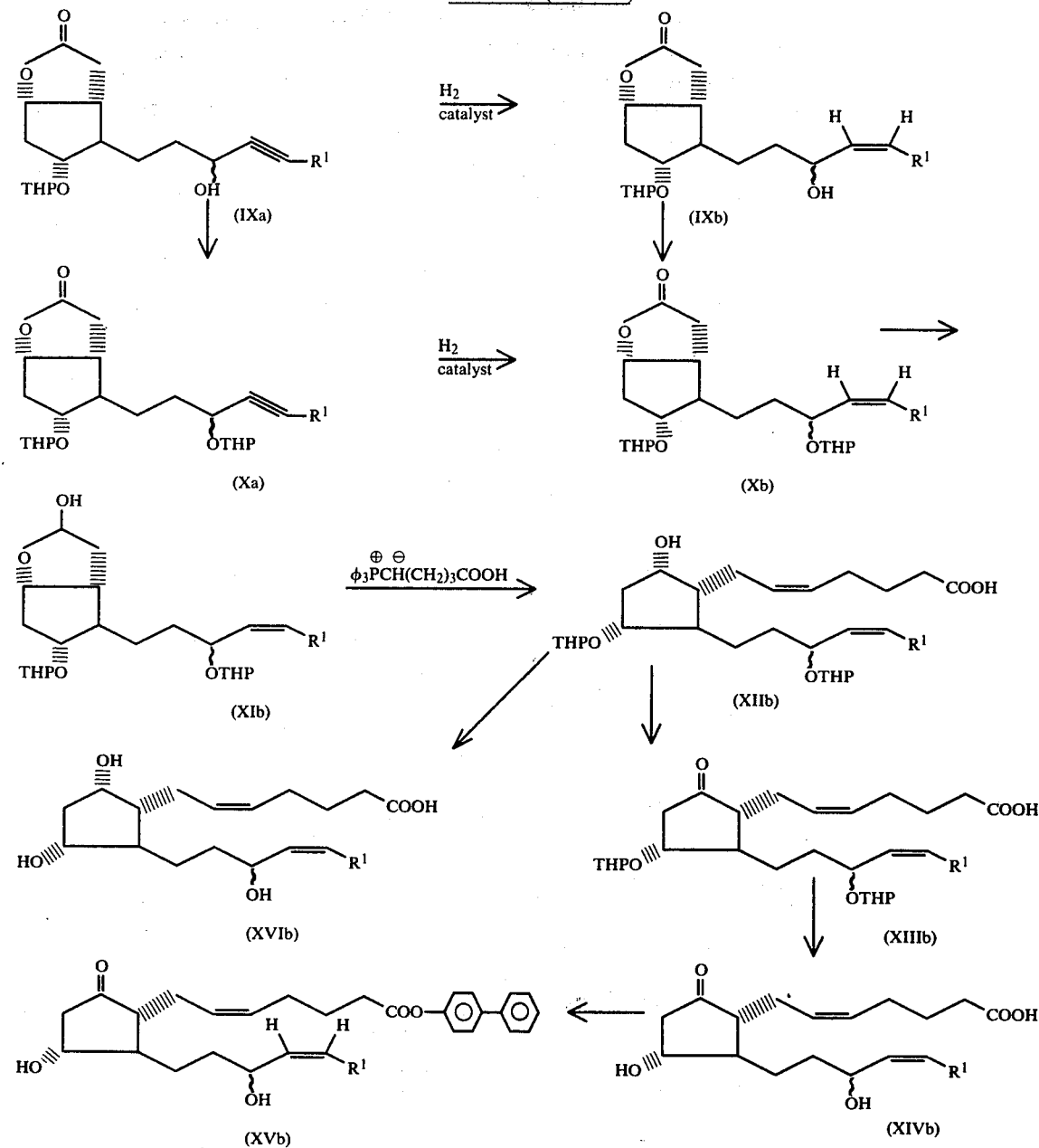

Scheme B (cis-16-enes)

The waved line attachment ( $\xi$ ) used herein indicates a mixture of the two possible configurations.
$\phi = C_6H_5$;
THP = 2-tetrahydropyranyl.

The process for preparing the cis-16-enes can utilize any of the compounds of formulae (IXa) through (XVIa) shown in Scheme A, above, that is any of the above compounds in which Z is —C≡C—. Such compounds can be contacted with hydrogen in the presence of any of the catalysts known in the art to selectively reduce an acetylenic group to a cis-olefin (see for example, Friefelder, op. cit., pp. 84–126 and references cited therein; and L. F. Fieser, "Reagents for Organic Synthesis," John Wiley and Sons, Inc., New York, 1968, pp. 566–567, and references cited therein) to obtain the corresponding compounds of formulae (IXb) through (XVIb). However, the preferred intermediates for use as starting material to prepare the cis-16-enes are the compounds of the formulae (IXa) and (Xa). Either of these acetylenic intermediates, when contacted with hydrogen in the presence of one of the selective catalysts, takes up an equimolar amount of hydrogen to provide the corresponding compounds of formulae (IXb) and (Xb). If a compound of formula (IXa) is employed as starting material, the hydrogenated product of formula (IXb) must then be treated to introduce the 2-tetrahydropyranyl hydroxyl protecting group by methods described above to obtain the novel intermediate of formula (Xb).

Examples of such catalysts which selectively reduce acetylenic groups to cis-olefins are lead poisoned palladium-on-calcium carbonate, lead poisoned palladium-on-barium carbonate, and either of the former in the presence of quinoline, isoquinoline or pyridine, nickel, including Raney nickel, iron, platinum and platinum oxide. The preferred catalyst is lead poisoned palladium-on-calcium carbonate, the so-called Lindlar catalyst, in the presence of quinoline.

In a typical experiment the starting material of formula (IXa) or (Xa) and catalytic amounts of the Lindlar catalyst and quinoline are combined in a reaction inert organic solvent such as benzene. The mixture is contacted with hydrogen at about atmospheric pressure. After the calculated amount of hydrogen [1 mole per mole of (IXa) or (Xa)] has been taken up, the mixture is filtered to remove catalyst and the solvent evaporated to provide the desired cis-olefin of formula (IXb) or (Xb). The product may be purified if desired, for example, by chromatography on silica gel.

The cis-olefins of formula (Xb), obtained as described above, are then carried through the same reaction steps as described above for the preparation of the corresponding acetylenic and trans-olefinic compounds to provide the novel intermediates of formulae (XIb), (XIIb), (XIIIb) and (XVIb) as well as the desired bronchodilators of formulae (XIVb) and (XVb).

The mixture of 15-hydroxy epimers of formula (II) wherein M is oxygen or

and $R^1$ and Z are as previously defined can be separated into the individual epimers (III) and (IV) as shown below.

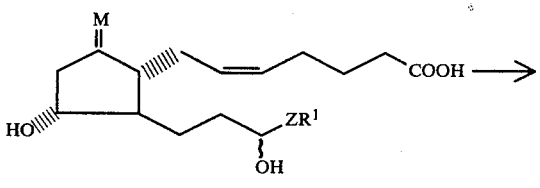

(II)

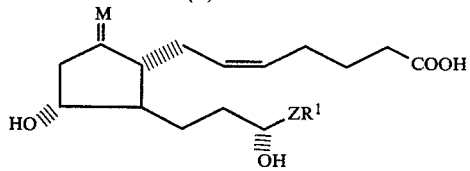

(III)

+

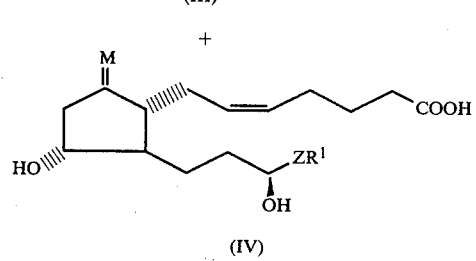

(IV)

The preferred method of separation of the above epimers is by chromatography on silica gel either by employing a column of silica gel or by preparative thin layer silica gel plates. Separations are efficient when elution is carried out with solvents such as ethyl ether optionally followed by mixtures of ethyl ether and ethyl acetate. By analogy with the natural prostaglandins, it is assumed that the slower moving epimers are those of formula (III), while the faster moving epimers are of formula (IV).

Compounds of the formula (II), (III) or (IV), above, may be reacted with active manganese dioxide under conditions known to selectively convert allylic or $\alpha,\beta$-acetylenic alcohols to ketones, as shown below, to provide the 15-keto compounds (V) wherein M, Z and $R^1$ have the values previously defined.

(II) 

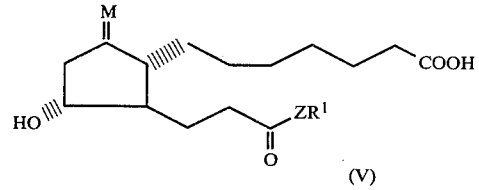

(V)

The preparation of the active manganese dioxide and its use for oxidation of allylic and $\alpha,\beta$-acetylenic alcohols has been previously described, see e.g., Stork et. al., Jour. Amer. Chem. Soc., 86, 471 (1964). The 15-keto compounds (V) wherein M is oxygen are also valuable selective bronchodilating agents.

As the literature cited under "Background of the Invention" establishes, the natural prostaglandins are known to exhibit a spectrum of physiological activities. In numerous in vivo and in vitro tests, all the compounds of formula (I) wherein R is hydrogen or biphenylyl; $R^1$ is a member selected from the group consisting of hydrogen, phenyl and alkyl having from one to eleven carbon atoms; Q is a member selected from the group consisting of oxygen,

and mixtures of

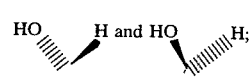

and Z is a member selected from the group consisting of —C≡C—,

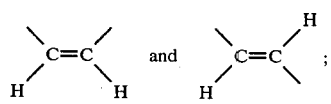

have been shown to have significant bronchodilator activity with greater selectivity of action than the natural prostaglandins. Said compounds of formula (I) are useful in mammals, including man, as bronchodilators. The above mentioned tests include a test for relative potency for spasmogenic effects on isolated guinea pig uterus, a test for effect on histamine and induced bronchospasm in the guinea pig, a test for effects on dog blood pressure, a test for relative potency for inducing diarrhea in mice and a test for relative potency for inhibition of gastric acidity in rats. These tests reveal that the compounds of formula (I) wherein $R^1$ is phenyl are also useful as antisecretory agents. Representative data are shown in Table I, below.

TABLE I

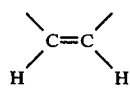

(XV)

| R[1] | Spasmogenic Effects[a] | Broncho-dilation[b] | Dog Blood Pressure[c] | Diarrhea[d] | Antisecretory[e] |
|---|---|---|---|---|---|
| where Z is —C≡C—: | | | | | |
| —CH$_2$CH$_2$CH$_3$ | 0.1 | 19 | 25 threshold 0.4 μg./Kg. | — | 33 |
| —CH$_2$(CH$_2$)$_2$CH$_3$ | — | 48 | 20 threshold 0.4 μg./Kg. | — | 0 |
| —CH$_2$(CH$_2$)$_3$CH$_3$ | 0.1 | 61 | 20 threshold 10 μg./Kg. | — | 30 |
| C$_6$H$_5$ | 5 | 3 | the acid was inactive at 20 μg./kg. | <10 | 28 |
| where ZR[1] is —CH=CH$_2$: | | | | | |
| | 0.01 | 32 | Inactive >20mg./Kg. | — | 0 |
| where Z is 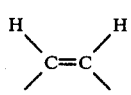: | | | | | |
| —CH$_2$CH$_2$CH$_3$ | 0.1 | 53 | 10 threshold 1.0 μg./Kg. | <10 | 40 |
| —CH$_2$(CH$_2$)$_2$CH$_3$ | 0.3 | 38 | 50 threshold 1.0 μg./Kg. | — | 60 |
| —CH$_2$(CH$_2$)$_3$CH$_3$ | 0.4 | 61 | 10 threshold 4 μg./Kg. | — | 10 |
| —C$_6$H$_5$ | 0.2 | 13 | 5 threshold 4.0 μg./Kg. | — | 33 |
| where Z is 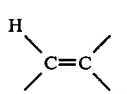: | | | | | |
| —CH$_2$(CH$_2$)$_3$CH$_3$ | — | 59 | — | — | 10 |

[a] Relative potency on isolated guinea pig uterus (PGE$_2$/PGF$_{2α}$ = 100).
[b] Approximate protection by equimolar aerosal dose on guinea pigs (100 μg./ml. PGE$_2$ ≃ 90-100)
[c] Relative potency (PGE$_2$/PGF$_{2α}$ = 100) for depressor effect on dog blood pressure.
[d] Relative potency for inducing diarrhea in mice (PGE$_2$ = 100).
[e] Relative potency for inhibition of pentagastrin stimulated gastric acid secretion in rats (PGE$_2$ = 100)

Particularly preferred selective bronchodilators of the invention are the compounds of formula (XV) wherein Z is —C≡C— and R[1] is either —CH$_2$CH$_2$CH$_3$ or —CH$_2$(CH$_2$)$_3$CH$_3$, those wherein Z is $$\overset{H}{\diagdown}C=C\overset{H}{\diagup}$$

and R[1] is —CH$_2$CH$_2$CH$_3$ or —CH$_2$(CH$_2$)$_3$CH$_3$ and those wherein Z is $$\overset{H}{\diagdown}C=C\overset{}{\diagdown}_{H}$$

and R[1] is —CH$_2$(CH$_2$)$_3$CH$_3$.

The compounds of formula (XV) wherein R[1] is C$_6$H$_5$ and Z is —C≡C— or $$\overset{}{\diagdown}C=C\overset{}{\diagup}_H$$

are examples of compounds of the invention having useful antisecretory activity.

As nasal decongestants, the aforesaid selective bronchodilators of formula (I) are used in a dose range of about 10 μg. to about 10 mg. per ml. of a pharmalogically suitable liquid vehicle such as aqueous alcohol or as an aerosol spray, both for topical application. They are also useful in controlling spasm and facilitating breathing in conditions such as bronchial asthma, bronchitis, bronchiectasis, pneumonia and emphysema. For these purposes, these compounds are administered in a variety of routes in a number of dosage forms, e.g., orally in the form of tablets, capsules, or liquids; rectally in the form of suppositories; parenterally with intravenous administration being preferred in emergency situations; by inhalation in the form of aerosols or solutions for nebulizers; or by insufflation in the form of powder.

Doses in the range of about 0.01 to 5 mg. per kg. of body weight are used 1 to 4 times a day. The compounds of the invention can also be combined advantageously with other anti-asthmatic agents, such as sympathomimetics (isoproterenol, phenylephrine, ephedrine, etc.); xanthine derivatives (theophylline and aminophyllin); and corticosteroids (ACTH and prednisolone).

As mentioned above, certain of the compounds of the invention are also useful antisecretory agents, and they may be used for this purpose in mammals, including man and animals to reduce and control excessive gastric secretion, thereby reducing or avoiding gastrointestinal ulcer formation, and accelerating the healing of such ulcers already present in the gastrointestinal tract. For this purpose, the compounds are administered orally, parenterally by injection or by intravenous infusion in an infusion dose range of about 0.1 μg. to about 500 μg. per kg. of body weight per minute, or in a total daily dose orally, by injection or infusion in the range of about 0.1 to about 20 mg. per kg. of body weight per day.

The following examples are merely illustrative, and in no way limit the scope of the appended claims. All temperatures are given in degrees Centigrade and all percentages are by weight unless otherwise indicated. Infrared absorption bands are reported in wave numbers ($cm^{-1}$). Nuclear magnetic resonance spectra ($^1H$-nmr) are measured at 60 MHz and peak positions are expressed in parts per million, ppm (δ) downfield from tetramethylsilane. The following abbreviations are used for peak shapes: b, broad; s, singlet; d, doublet; t, triplet; q, quartet; m, multiplet.

EXAMPLE 1

2-[5α-Hydroxy-3α(tetrahydropyran-2-yloxy)-2β-(2-formylvinyl) cyclopent-1α-yl]acetic acid, γ-lactone(VII)

To a solution of 3 g. (11 mmole) 2-[5α-Hydroxy-3α-(tetrahydropyran-2-yloxy)-2β-formylcyclopent-1α-yl]acetic acid, γ-lactone(VI), [prepared by the procedure of Corey et al., *J. Am. Chem. Soc.*, 93, 1490 (1971)] in 20 ml. of anhydrous methylene chloride was added dropwise (over 20 minutes) a solution of 2 g (11 mmole) formylmethylene dimethylphenyl phosphonium ylid.*
After complete addition, the reaction was flushed with nitrogen and placed in a freezer (−20°) overnight.
*Preparation of formylmethylene dimethyl phenylphosphonium ylid: To a cold (0°) suspension of 9.32 g. (0.04 mole) phenyl trimethylphosphonium bromide in 100 ml. of anhydrous tetrahydrofuran was added dropwise 19 ml. (0.04 mole) n-butyl lithium (Alfa Inorganics). The resulting yellow solution was stirred for 20 minutes under nitrogen at 0°. A solution of 9.4 ml. of ethyl formate in 30 ml. of tetrahydrofuran was then added in a steady stream (a white solid forms). The reaction was stirred for an additional 30 minutes, poured onto 100 ml. of cold 1 N hydrochloric acid and washed with ether. The aqueous layer was basified with 40% aqueous sodium hydroxide and repeatedly (over 6 hours extracted with $CH_2Cl_2$. The combined $CH_2Cl_2$ extracts were washed with a small amount of water, dried ($Na_2SO_4$) and evaporated to give 2±0.5 g. of ylid as an unstable yellow solid. The reaction mixture was then diluted with methylene chloride and washed with water. The organic layer was dried ($Na_2SO_4$) and evaporated to yield 4.3 g. of crude material which was purified by chromatography on 120 g. of silica gel (Baker "Analyzed" Reagent). After elution of high R$_f$ impurities, the product, 1.5 g., was collected. $^1H$-nmr (CDCl$_3$)ppm (δ): 1.20-3.12 and 3.12-4.35 (two multiplets, 15), 4.62 (s,1), 4.80-5.15 (m,1), 5.84-7.00 (m,2, olefinic protons), 9.75 (d,1,CHO). IR (CHCl$_3$) cm$^{-1}$: 1775 (lactone), 1690 (aldehyde).

EXAMPLE 2

2-[5α-Hydroxy-3α-(tetrahydropyran-2-yloxy)-2β-(2-formylethyl)cyclopent-1α-yl]acetic acid, γ-lactone (VIII)

A solution of 1.1 g. (3.5 mmole) 2-[5α-hydroxy-3α-(tetrahydropyran-2-yloxy)-2β-(2-formylvinyl)cyclopent-1α-yl]acetic acid, γ-lactone (VII) in 30 ml. of absolute ethanol containing 300 mg. of 5% Pd/C catalyst was hydrogenated at 15 psi for 20 minutes (hydrogen uptake was 100 ml). The reaction was filtered and evaporated to give 1.1 g. of crude product which was purified by chromatography on 30 g. silica gel (Baker "Analyzed" Reagent 60–200 mesh). After elution of high R$_f$ impurities the fractions containing the title compound were collected and evaporated to obtain 800 mg. $^1H$-nmr (CDCl$_3$)ppm(δ): 0.64–2.85 and 3.00–4.13 (two multiplets, 19), 4.60 (s, 1), 4.72–5.17 (m, 1), 9.30 (s, 1, CHO). IR (CHCl$_3$)cm$^{-1}$:1770 (lactone), 1730 (aldehyde)

EXAMPLE 3

2-[5α-Hydroxy-3α-(tetrahydropyran-2-yloxy)-2β-(3-hydroxy-5-phenyl-4-pentyne-1-yl)cyclopent-1α-yl]acetic acid, γ-lactone (IXa, $R^1=C_6H_5$)

To a solution of 1.66 g. (6 mmole) 2-[5α-hydroxy-3α-(tetrahydropyran-2-yloxy)-2β-(2-formylethyl)cyclopent-1α-yl]acetic acid, γ-lactone (VIII) in 70 ml. of anhydrous tetrahydrofuran at −78° in a dry nitrogen atomsphere was added dropwise 18.3 ml. (9 mmole) 0.49 M lithium phenylacetylide* in tetrahydrofuran. The reaction was stirred at −78° for 20 minutes then poured onto 200 ml. of ether/ethyl acetate (50/50) containing ice-water. The organic layer was separated, washed with brine, dried ($Na_2SO_4$) and evaporated to give 2.2 g. crude product which was purified by column chromatography on 150 g. of silica gel (Baker "Analyzed" Reagent 60–200 mesh). After elution of high R$_f$ impurities, 1.4 g. of the title compound was collected. $^1H$-nmr (CDCl$_3$) ppm (δ):1.10–3.10 and 3.20–4.51 (two multiplets, 20), 4.40–4.82 (m, 2), 4.82–5.20 (bs, 1), 7.35 (s, 5, $C_6H_5$). IR (CHCl$_3$) cm$^{-1}$:1770 (lactone) 3600 (hydroxyl).
*The lithium phenylacetylide was prepared in the following way. To a cold (0°) solution of 2.04 g. (20 mmole) phenylacetylene in 20 ml. of toluene containing 10 ml. of anhydrous tetrahydrofuran was added 9.4 ml. (20 mmole) 2.2 M n-butyl lithium (Alfa Inorganics). The resulting pale yellow solution was stirred at 0° for 20 minutes, then titrated and found to be 0.49 Molar.

EXAMPLE 4

2-[5α-Hydroxy-3α-(tetrahydropyran-2-yloxy)-2β-(3-{tetrahydropyran-2-yloxy}-5phenyl-4-pentyne-1-yl)cyclopent-1α-yl]acetic acid, γ-lactone (Xa, $R^1=C_6H_5$)

To a cold (−10°) solution of 2.5 g. (6.5 mmole) 2-[5α-Hydroxy-3α-(tetrahydropyran-2-yloxy)-2β-(3-hydroxy-5-phenyl-4-pentyne-1-yl)cyclopent-1α-yl]acetic acid, γ-lactone (IXa, $R^1=C_6H_5$) in 30 ml. anhydrous methylene chloride containing 815 mg. (9.7 mmole) 2,3-dihydropyran was added 25 mg. p-toluenesulfonic acid monohydrate. After stirring for 3 hours at −10°, the reaction was poured onto ether (150 ml.), washed with aqueous sodium bicarbonate (20 ml.), dried ($Na_2SO_4$) and evaporated to give 3.3 g. of the title compound of sufficient purity for use in the next step.

EXAMPLE 5

2-[5α-Hydroxy-3α-(tetrahydropyran-2-yloxy)-2β-(3-{tetrahydropyran-2-yloxy}-5-phenyl-4-pentyne-1-yl)cyclopent-1α-yl]-acetaldehyde, γ-hemiacetal (XIa, $R^1=C_6H_5$)

A solution of 3.3 g. (7.05 mmole) 2-[5α-Hydroxy-3α-(tetrahydropyran-2-yloxy)-2β-(3-{tetrahydropyran-2-yloxy}-5-phenyl-4-pentyne-1-yl)cyclopent-1α-yl]acetic acid, γ-lactone (Xa, $R^1=C_6H_5$) in 70 ml. anhydrous toluene was cooled to −78° in a dry nitrogen atmosphere. To this cooled solution was added 9.6 ml. (7.7 mmole) of 20% diisobutylaluminum hydride in n-hexane (Alfa Inorganics) dropwise over 20 minutes at such a rate that the temperature remained below −66°. After an additional 45 minutes of stirring at −78°, the reaction mixture was diluted with ether (300 ml.). The ether solution was washed with 50% (w/w) sodium potassium tartrate solution (2×50 ml.), dried (MgSO$_4$) and concentrated to yield 3.5 g. crude product which was purified by column chromatography on 150 g. of silica gel (Baker "Analyzed" Reagent 60–200 mesh). The yield of pure title compound was 2.4 g.

EXAMPLE 6

9α-Hydroxy-11α-(tetrahydropyran-2-yloxy)-15-(tetrahydropyran-2-yloxy)-17-phenyl-ω-trinor-prosta-cis-5-ene-16-yneoic acid (XIIa, R$^1$=C$_6$H$_5$)

To a solution of 6.65 g. (15 mmole) (4-carboxy-n-butyl)triphenylphosphonium bromide in 10 ml. of anhydrous dimethylsulfoxide in a dry nitrogen atmosphere was added 18 ml. (28.5 mmole) of a 1.58 M solution of sodium methylsulfinylmethide in dimethylsulfoxide. To this red ylide solution at 40° (oil bath) was added dropwise a solution of 2 g. (4.25 mmole) 2-[5α-hydroxy-3α-(tetrahydropyran-2-yloxy)-2β-(3-{tetrahydropyran-2-yloxy}-5-phenyl-4-pentyne-1-yl)cyclopent-1α-yl]acetaldehyde, γ-hemiacetal (XIa, R$^1$=C$_6$H$_5$) in 10 ml. of dry dimethylsulfoxide over a period of 10 minutes. After 45 minutes at 40°, the reaction was poured onto ice water. The basic aqueous solution (200 ml.) was covered with ethyl acetate (200 ml.) and with vigorous stirring was acidified to pH∼3 with 1 N aqueous hydrochloric acid. The acidic solution was extracted with ethyl acetate 82×200 ml.) and the combined organic extracts washed with saturated brine, dried (Na$_2$SO$_4$) and evaporated to a solid residue which was triturated with ether and filtered. The filtrate was concentrated and purified by column chromatography on 175 g. silica gel (Baker "Analyzed" Reagent 60–200 mesh). After removal of less polar impurities, the fractions containing the title compound were combined and evaporated to dryness to obtain 1.8 g. of purified product.

EXAMPLE 7

9-oxo-11α-(tetrahydropyran-2-yloxy)-15-(tetrahydropyran-2-yloxy)-17-phenyl-ω-trinor-prosta-cis-5-ene-16-yneoic acid (XIIIa, R$^1$=C$_6$H$_5$)

To a solution of 554 mg. (1 mmole) 9α-Hydroxy-11α-(tetrahydropyran-2-yloxy)-15-(tetrahydropyran-2-yloxy)-17-phenyl-ω-trinor-prosta-cis-5-ene-16-yneoic acid (XIIa, R$^1$=C$_6$H$_5$) in 20 ml. of acetone at −10° in a dry nitrogen atmosphere was added 0.42 ml. (1.1 mmole) of 2.67 M. Jones' reagent [see, e.g., Jour. Chem. Soc., 3019 (1953)]. After 10 minutes at −10°, the reaction was poured onto ethyl acetate (75 ml.), washed with water (1×25 ml.), dried (Na$_2$SO$_4$) and concentrated to yield 530 mg. of the desired product.

EXAMPLE 8

9-oxo-11α,15-dihydroxy-17-phenyl-ω-trinor-prosta-cis-5-ene-16-yneoic acid (XIVa, R$^1$=C$_6$H$_5$)

A solution of 530 mg. crude 9-oxo-11α-(tetrahydropyran-2-yloxy)-15-(tetrahydropyran-2-yloxy)-17-phenyl-ω-trinor-prosta-cis-5-ene-16-yneoic acid (XIIa, R$^1$=C$_6$H$_5$) in 10 ml. of a 65:35 mixture of glacial acetic acid/water was stirred under nitrogen at 27° overnight, then concentrated by rotary evaporation at reduced pressure. The resultant crude oil was purified by chromatography on 30 g. silica gel (MallincKrodt CC-7 100–200 mesh). After elution of less polar impurities, the 9-oxo-11α,15-dihydroxy-17-phenyl-ω-trinor-prosta-cis-5-ene-16-yneoic acid, weighing 120 mg., was collected. IR (CHCl$_3$) cm$^{-1}$:1710 (COOH), 1740 (ketone), 3600 (hydroxyl).

EXAMPLE 9

9α,11α,15-trihydroxy-17-phenyl-ω-trinor-prosta-cis-5-ene-16-yneoic acid (XVIa, R$^1$=C$_6$H$_5$)

A solution of 250 mg. 9α-hydroxy-11α-(tetrahydropyran-2-yloxy)-15-(tetrahydropyran-2-yloxy)-17-phenyl-ω-trinor-prosta-cis-5-ene-16-ynoic acid (XIIa, R$^1$=C$_6$H$_5$) in 5 ml. of a 65:35 mixture of glacial acetic acid/water was stirred under nitrogen at 27° overnight, then concentrated in vacuo by rotary evaporation. The resultant crude oil was purified by chromatography on 25 g. silica gel (Mallinckrodt CC-7 100–200 mesh). After elution of less polar impurities fractions containing 60 mg. of the title compound were collected and evaporated to dryness. IR(CHCl$_3$)cm$^{-1}$: 1710(COOH), 3600(hydroxyl).

EXAMPLE 10

2-[5α-Hydroxy-3α-(tetrahydropyran-2-yloxy)-2β-(3-(tetrahydropyran-2-yloxy)-2β-(3-hydroxy-5-phenyl-pent-cis-4-ene-1-yl)cyclopent-1α-yl]acetic acid, γ-lactone (IXb, R$^1$=C$_6$H$_5$)

A solution of 1.47 g. (3.85 mmole) 2-[5α-hydroxy-3α-(tetrahydropyran-2-yloxy)-2β-(3-hydroxy-5-phenyl-4-pentyn-1-yl)cyclopent-1α-yl]acetic acetic acid, γ-lactone (IXa, R$^1$=C$_6$H$_5$) in 40 ml. of anhydrous benzene containing 4 drops of quinoline was hydrogenated at atmospheric pressure over 260 mg. of Lindlar catalyst. After 2 hours the rate of hydrogen uptake stopped (73 ml. H$_2$ had been absorbed). The reaction mixture was filtered and evaporated to give 1.5 g. of crude product which was purified by column chromatography on 100 g. silica gel (Baker "Analyzed" Reagent 60–200 mesh). The yield of purified title compound was 1.33 g. $^1$H-nmr (CDCl$_3$) ppm (δ): 1.10–3.20 (m, 20), 4.20–4.80 (m, 2), 4.80–5.18 (bs, 1), 5.65 (t, 1, olefinic proton), 6.50 (d, 1, olefinic proton), 7.34 (s, 5, C$_6$H$_5$). IR (CHCl$_3$) cm$^{-1}$: 1770 (lactone), 3600 (hydroxyl).

EXAMPLE 11

2-[5α-Hydroxy-3α-tetrahydropyran-2-yloxy)-2β-(3-{tetrahydropyran-2-yloxy}-5-phenyl-pent-cis-4-ene-1-yl)cyclopent-1α-yl]acetic acid, γ-lactone (Xb, R$^1$=C$_6$H$_5$)

To a solution of 1.6 g. (4.15 mmole) 2-[5α-hydroxy-3α(tetrahydropyran-2-yloxy)-2β-(3-hydroxy-5-phenyl-pent-cis-4-ene-1-yl)cyclopent-1α-yl]acetic acid, γ-lactone (IXb, R$^1$=C$_6$H$_5$) in 30 ml. anhydrous methylene chloride containing 0.5 ml. (6.6 mmole) of 2,3-dihydropyran at 0° in a dry nitrogen atmosphere was added 30 mg. p-toluenesulfonic acid monohydrate. After stirring for 40 minutes at 0°, the reaction was poured onto ether (200 ml.). The ether solution was washed with saturated sodium bicarbonate (1×50 ml.) then saturated brine (1×50 ml.), dried (Na$_2$SO$_4$) and concentrated to yield 2.0 g. of the desired product.

EXAMPLE 12

2-[5α-Hydroxy-3α-(tetrahydropyran-2-yloxy)-2β-(3-{tetrahydropyran-2-yloxy}-5-phenyl-pent-cis-4-ene-1-yl)cyclopent-1α-yl]acetaldehyde, γ-hemiacetal (XIb, $R^1=C_6H_5$)

A solution of 2.0 g. (4.25 mmole) 2-[5α-hydroxy-3α-(tetrahydropyran-2-yloxy)-2β-{3-tetrahydropyran-2-yloxy}-5-phenyl-pent-cis-4-ene-1-yl)cyclopent-1α-yl]acetic acid, γ-lactone (Xb, $R^1=C_6H_5$) in 35 ml. anhydrous toluene was cooled to −78° in a dry nitrogen atmosphere. To this cooled solution was added 5.9 ml. (4.7 mmole) of 20% diisobutylaluminum hydride in n-hexane (Alfa Inorganics) dropwise over 20 minutes at such a rate that the temperature remained below −66°. After an additional 45 minutes of stirring at −78°, the reaction was diluted with ether (250 ml.). The ether solution waas washed with 50% (w/w) sodium potassium tartrate solution (2×50 ml.), dried (MgSO4) and concentrated to yield 2.3 g. of the crude title compound which was purified by column chromatography on 125 g. of silica gel (Baker "Analyzed" Reagent). The yield of pure product was 1.7 g. (85%).

EXAMPLE 13

9α-Hydroxy-11α-(tetrahydropyran-2-yloxy)-15-(tetrahydropyran-2-yloxy)-17-phenyl-ω-trinor-prosta-cis-5,16-dienoic acid (XIIb, $R^1=C_6H_5$)

To a solution of 3.24 g. (7.32 mmole) (4-carboxy-n-butyl)triphenylphosphonium bromide 15 ml of anhydrous dimethylsulfoxide in a dry nitrogen atmosphere was added 7.7 ml. (13.9 mmole) of a 1.8 M solution of sodium methylsulfinylmethide in dry dimethylsulfoxide. To this red ylid solution at 40° (oil bath) was added dropwise a solution 1.15 g. (2.44 mmole) 2-[5α-hydroxy-3α-(tetrahydropyran-2-yloxy)-2β-(3-{tetrahydropyran-2-yloxy}-5-phenyl-pent-cis-4-ene-1-yl)cyclopent-1α-yl]acetaldehyde, γ-hemiacetal (XIb, $R^1=C_6H_5$) in 10 ml. of dry dimethylsulfoxide over a period of 10 minutes. After 45 minutes at 40°, the reaction was poured onto ice water. The basic aqueous solution (150 ml.) was covered with ethyl acetate (150 ml.) and with vigorous stirring was acidified to pH ~3 with 1 N aqueous hydrochloric acid. The acidic solution was extracted with ethyl acetate (2×75 ml.) and the combined organic extracts washed with saturated brine, dried (Na2SO4) and evaporated to a solid residue which was triturated with ether and filtered. The filtrate was concentrated and purified by column chromatography on 100 g. silica gel (Baker "Analyzed" Reagent 60-200 mesh). After removal of high $R_f$ impurities, 1.1 g. of pure title compound was collected.

EXAMPLE 14

9-oxo-11α-(tetrahydropyran-2-yloxy)-15-(tetrahydropyran-2-yloxy)17-phenyl-ω-trinor-prosta-cis-5,16-dienoic acid (XIIIb, $R^1=C_6H_5$)

To a solution of 733 mg. (1.4 mmole) 9α-hydroxy-11α-(tetrahydropyran-2-yloxy)-15-tetrahydropyran-2-yloxy)-17-phenyl-ω-trinor-prosta-cis-5,16-dienoic acid in 60 ml. of acetone at −10° in a dry nitrogen atmosphere was added 0.6 ml. (1.5 mmole) of 2.67 M. Jones' reagent. After 10 minutes at −10°, the reaction was poured onto ethyl acetate (200 ml.), washed with water (2×50 ml.), dried (Na2SO4) and concentrated to yield 800 mg. crude 9-oxo-11α-(tetrahydropyran-2-yloxy)-15-(tetrahydropyran-2-yloxy)-17-phenyl-ω-trinor-prosta-cis-5,16-dienoic acid.

EXAMPLE 15

9-oxo-11α,15-dihydroxy-17-phenyl-ω-trinor-prosta-cis-5,16-dienoic acid (XIVb, $R^1=C_6H_5$)

A solution of 830 mg. of the product of Example 14 (XIIIb, $R^1=C_6H_5$), in 20 ml. of a 65:35 mixture of glacial acetic acid/water was stirred under nitrogen at 27° overnight, then concentrated by rotary evaporation. The resultant crude oil was purified by chromatography on 45 g. silica gel (Mallinckrodt CC-7 100-200 mesh). After elution of less polar impurities, fractions containing 320 mg. of 9-oxo-11α-15-dihydroxy-17-phenyl-ω-trinor-prosta-cis-5,16-dienoic acid were collected. $^1$H-nmr (CDCl3) ppm (δ): 1.00-2.64 and 3.72-4.30 (two multiplets, 16), 4.30-4.83 (m, 1), 5.00-6.00 (m, 6, three olefinic protons, two hydroxyl protons and COOH), 6.50 (d, 1, olefinic proton), 7.28 (s, 5, $C_6H_5$). IR (CHCl3) cm$^{-1}$: 1710 (COOH), 1740 (ketone), 3600 (hydroxyl).

EXAMPLE 15A

9α,11α,15-Trihydroxy-17-phenyl-ω-trinor-cis-5,16dienoic acid (XVIb, $R^1=C_6H_5$)

By employing 9α-hydroxy-11α(tetrahydropyran-2-yl-oxy)-15-(tetrahydropyran-2-yloxy)-17-phenyl-ω-trinor-prosta-cis-5,16-dienoic acid (XIIb, $R^1=C_6H_5$) in place of the corresponding 9-oxo compound (XIIIb, $R^1=C_6H_5$) in the above hydrolysis procedure the title compound is similarly obtained.

EXAMPLE 16

9-oxo-11α,15-dihydroxy-17-phenyl-ω-trinor-prosta-cis-5,16-dienoic acid, p-biphenylyl ester (XVb, $R^1=C_6H_5$)

To a partial solution of 1.2 g. (7 mmole) p-phenylphenol in 20 ml. anhydrous methylene chloride in a dry nitrogen atmosphere was added 270 mg. (0.7 mmole) 9-oxo-11α,15-dihydroxy-17-phenyl-ω-trinor-prosta-cis-5,16-dienoic acid (XVIb, $R^1=C_6H_5$). A solution of 226 mg. (1.1 mmole) dicyclohexylcarbodiimide in 5 ml. anhydrous methylene chloride was then added dropwise over one hour. After stirring an additional 30 minutes at room temperature, the solvent was evaporated and the residue purified by column chromatography on 55 g. silica gel (Baker "Analyzed" Reagent 60-200 mesh). After elution of high $R_f$ impurities, fractions containing 200 mg. of the title compound were collected. The melting point was 106°-123°.

EXAMPLE 16A

9-Oxo-11α,15-dihydroxy-17-phenyl-ω-trinor-prosta-cis-5-ene-16-yneoic acid biphenylyl ester By employing the above procedure, but replacing the 9-oxo-11α,15-dihydroxy-17-phenyl-ω-trinor-prosta-cis-5,16-dienoic acid used therein with an equimolar amount of the product obtained in Example 8 affords the title compound, M.P. 95°-109°.

EXAMPLE 17

2-[5α-Hydroxy-3α-(tetrahydropyran-2-yloxy)-2β-(3-hydroxy-oct-4-yl-1-yl)-cyclopent-1α-yl]acetic acid, γ-lactone (IXa, $R^1=n-C_3H_7$)

To a solution of 2.3 g. (8 mmole) 2-[5α-hydroxy-3α-(tetrahydropyran-2-yloxy)-2β-(2-formylethyl)cyclopent-1α-yl]acetic acid, γ-lactone (VIII) in 120 ml. of anhydrous tetrahydrofuran at −78° in a dry nitrogen atmosphere was added dropwise 50 ml. (20 mmole) 0.49 M lithium pentylide* in tetrahydrofuran. The reaction was stirred at −78° for 20 minutes then poured onto 200 ml. of ether/ethyl acetate (50/50) containing ice-water. The organic layer was separated, washed with brine, dried ($Na_2SO_4$) and evaporated to give 4.0 g. crude product which was purified by column chromatography on 120 g. of silica gel (Baker "Analyzed" Reagent) yielding 1.7 g. of pure title compound. $^1$H-nmr ($CDCl_3$) ppm (δ): 1.00 (t, 3, $CH_3$), 1.25–4.65 (multiplets, 25), 4.65–4.88 (s, 1), 4.88–5.25 (bs, 1). IR ($CHCl_3$)cm$^{-1}$: 1770 (lactone), 3600 (hydroxyl).

*The lithium pentylide was prepared in the following way: To a cold (0°) solution of 1 g. (14.6 mmole) 1-pentyne in 20 ml. of toluene containing 10 ml. of anhydrous tetrahydrofuran was added 5.8 ml. (1.4 mmole) 2.47 M butyl lithium (Alfa Inorganics). The resulting pale yellow solution was stirred at 0° for 20 minutes, then titrated and found to be 0.49 Molar.

EXAMPLE 17A

When the above procedure is repeated but using an equimolar amount of the appropriate lithium acetylide ($Li^+$ $^-C{\equiv}C$-$R^1$) in place of lithium pentylide in each case, the following compounds of formula (IXa) are similarly obtained.

| $R^1$ | Yield, % |
|---|---|
| —$CH_2(CH_2)_2CH_3$ | 60 |
| —$CH_2(CH_2)_3CH_3$ | 56 |
| H | — |
| $CH_3$ | — |
| —$CH_2(CH_2)_4CH(CH_3)_2$ | — |
| —$CH_2CH(CH_2)_7CH_3$<br>    \|<br>   $CH_3$ | — |

EXAMPLE 18

2-[5α-Hydroxy-3α-(tetrahydropyran-2-yloxy)-2β-(3{tetrahydropyran-2-yloxy}-oct-4-yne-1-yl)cyclopent-1α-yl]acetic acid, γ-lactone (Xa, $R^1$=n-$C_3H_7$)

To a solution of 1.68 g. (4.8 mmole) 2-[5α-hydroxy-3α-(tetrahydropyran-2-yloxy)-2β-(3-hydroxy-oct-4-yne-1-yl)cyclopent-1α-yl]acetic acid, γ-lactone (IXa, $R^1$=n-$C_3H_7$) in 60 ml. anhydrous methylene chloride containing 0.55 ml. (7.3 mmole) of 2,3-dihydropyran at 0° in a dry nitrogen atmosphere was added 30 mg. p-toluenesulfonic acid monohydrate. After stirring for 40 minutes at 0°, the reaction was poured onto ether (200 ml.). The ether solution was washed with saturated sodium bicarbonate (1×50 ml.) then saturated brine (1×50 ml.), dried ($Na_2SO_4$) and concentrated to yield 2.12 g. of crude product.

EXAMPLE 18A

When the products prepared in Example 17A are employed in the procedure of Example 18 in place of 2-[5α-hydroxy-3α-(tetrahydropyran-2-yloxy)-2β-(3-hydroxy-oct-4-yne-1-yl)cyclopent-1-yl]acetic acid, γ-lactone, the following compounds of formula (Xa) are obtained.

| $R^1$ | Yield, % |
|---|---|
| —$CH_2(CH_2)_2CH_3$ | 93 |
| —$CH_2(CH_2)_3CH_3$ | 100 |
| H | — |
| $CH_3$ | — |
| —$CH_2(CH_2)_4CH(CH_3)_2$ | — |
| —$CH_2CH(CH_2)_7CH_3$<br>    \|<br>   $CH_3$ | — |

EXAMPLE 19

2-[5α-Hydroxy-3α-(tetrahydropyran-2-yloxy)-2β-(3-{tetrahydropyran-2-yloxy}-oct-4-yne-1-yl)cyclopent-1α-yl]acetaldehyde, γ-hemiacetal (XIa, $R^1$=n-$C_3H_7$)

A solution of 2.2 g. (4.9 mmole) 2-[5α-hydroxy-3α-(tetrahydropyran-2-yloxy)-2β-(3-{tetrahydropyran-2-yloxy}-oct-4-yne-1-yl)cyclopent-1α-yl]-acetic acid, γ-lactone (Xa, $R^1$=n-$C_3H_7$) in 40 ml. anhydrous toluene was cooled to −78° in a dry nitrogen atmosphere. To this cooled solution was added 6.8 ml. (5.4 mmole) of 20% diisobutylaluminum hydride in n-hexane (Alfa Inorganics) dropwise at such a rate that the temperature remained below −66°. The addition required 20 minutes. After an additional 45 minutes of stirring at −78°, the reaction was diluted with ether (200 ml.). The ether solution was washed with 50% (w/w) sodium potassium tartrate solution (2×50 ml.), dried ($MgSO_4$) and concentrated to yield 2.3 g. of crude material which was purified by column chromatography on 100 g. of silica gel (Baker "Analyzed Reagent). The yield of pure title compound was 1.46 g.

EXAMPLE 19A

When the products of Example 18A are employed in the above procedure in place of 2-[5α-hydroxy-3α-(tetrahydropyran-2-yloxy)-2β-(3-[tetrahydropyran-2-yloxy]-oct-4-yne-1-yl)cyclopent-1α-yl]acetic acid, γ-lactone, the following compounds are likewise obtained.

| $R^1$ | Yield, % |
|---|---|
| —$CH_2(CH_2)_2CH_3$ | 100 |
| —$CH_2(CH_2)_3CH_3$ | 67 |
| H | — |
| $CH_3$ | — |
| —$CH_2(CH_2)_4CH(CH_3)_2$ | — |

-continued (XIa)

| $R^1$ | Yield, % |
|---|---|
| —CH$_2$CH(CH$_2$)$_7$CH$_3$<br>      |<br>     CH$_3$ | — |

EXAMPLE 20

9α-Hydroxy-11α-(tetrahydropyran-2-yloxy)-15-(tetrahydropyran-2-yloxy)-prosta-cis-5-ene-16-yneoic acid (XIIa, $R^1$=n-C$_3$H$_7$)

To a solution of 4.08 g. (9.2 mmole) (4-carboxy-n-butyl)triphenylphosphonium bromide 14 ml. of anhydrous dimethylsulfoxide in a dry nitrogen atmosphere was added 9.7 ml. (17.5 mmole) of a 1.80 M solution of sodium methylsulfinylmethide in dry dimethylsulfoxide. To this red ylide solution at 40° (oil bath) was added dropwise a solution of 1.0 g. (2.3 mmole) 2-[α-hydroxy-3α-(tetrahydropyran-2-yloxy)-2β-(3-{tetrahydropyran-2-yloxy}-oct-4-yne-1-yl)cyclopent-1α-yl]acetaldehyde, γ-hemiacetal (XIa, $R^1$=n-C$_3$H$_7$) in 9 ml. of dry dimethylsulfoxide over a period of 10 minutes. After 45 minutes at 40°, the reaction was poured onto ice water. The basic aqueous solution (150 ml.) was covered with ethyl acetate (150 ml) and with vigorous stirring was acidified to pH~3 with 1 N aqueous hydrochloric acid. The acidic solution was extracted with ethyl acetate (2×150 ml.) and the combined organic extracts washed with saturated brine, dried (Na$_2$SO$_4$) and evaporated to a solid residue which was triturated with ether and filtered. The filtrate was concentrated and purified by column chromatography on 100 g. silica gel (Baker "Analyzed" Reagent 60–200 mesh). After removal of high R$_f$ impurities, 1.05 g. of 9α-hydroxy-11α-(tetrahydropyran-2-yloxy)-15-(tetrahydropyran-2-yloxy)-prosta-cis-5-ene-16-yneoic acid was collected.

EXAMPLE 20A

When the products of Example 19A are employed in the above procedure in place of the 2-[5α-hydroxy-3α-(tetrahydropyran-2-yloxy)-2β-(3-{tetrahydropyran-2-yloxy}-oct-4-yne-1-yl)cyclopent-1α-yl]acetaldehyde, γ-hemiacetal used therein, the following compounds of formula (XIIa) are obtained.

(XIIa)

| $R^1$ | Yield, % |
|---|---|
| —CH$_2$(CH$_2$)$_2$CH$_3$ | 83 |
| —CH$_2$(CH$_2$)$_3$CH$_3$ | 79 |
| H | — |
| CH$_3$ | — |
| —CH$_2$(CH$_2$)$_4$CH(CH$_3$)$_2$ | — |

(XIIa)

| $R^1$ | Yield, % |
|---|---|
| —CH$_2$CH(CH$_2$)$_7$CH$_3$<br>      |<br>     CH$_3$ | — |

EXAMPLE 21

9-oxo-11α-(tetrahydropyran-2-yloxy)-15-(tetrahydropyran-2-yloxy)-prosta-cis-5-ene-16-yneoic acid (XIIIa, $R^1$=n-C$_3$H$_7$)

To a solution of 733 mg. (1.4 mmole) 9α-hydroxy-11α-(tetrahydropyran-2-yloxy)-15-(tetrahydropyran-2-yloxy)-prosta-cis-5-ene-16-yneoic acid (XIIa, $R^1$=n-C$_3$H$_7$) in 60 ml. of acetone at −10° in a dry nitrogen atmosphere was added 6 ml. (1.6 mmole) of 2.67 M Jones' reagent. After 10 minutes at −10°, the reaction was poured onto ethyl acetate (100 ml.), washed with water (1×25 ml.), dried (Na$_2$SO$_4$) and concentrated to yield 800 mg. the crude title compound.

EXAMPLE 21A

When the compounds obtained in Example 20A are employed as starting material in place of the 9α-hydroxy-11α-(tetrahydropyran-2-yloxy)-15-(tetrahydropyran-2-yloxy)-prosta-cis-5-ene-16-yneoic acid in the procedure of Example 21, the following compounds are obtained.

| $R^1$ | Yield, % |
|---|---|
| —CH$_2$(CH$_2$)$_2$CH$_3$ | 97 (crude) |
| —CH$_2$(CH$_2$)$_3$CH$_3$ | 100 (crude) |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>      |<br>     CH$_3$ | — |

EXAMPLE 22

9-oxo-11α,15-dihydroxyprosta-cis-5-ene-16-yneoic acid (XIVa, $R^1$=n-C$_3$H$_7$)

A solution of 800 mg. 9-oxo-11α-(tetrahydropyran-2-yloxy)-15-(tetrahydropyran-2-yloxy)prosta-cis-5-ene-16-yneoic acid (XIIIa, $R^1$=n-C$_3$H$_7$) in 20 ml. of a 65:35 mixture of glacial acetic acid/water was stirred under nitrogen at 27° overnight, then concentrated in vacuo by rotary evaporation. The resultant crude oil was purified by chromatography on 45 g. silica gel (Mallinckrodt CC-7 100–200 mesh). After elution of less polar impurities the 9-oxo-11α,15-dihydroxy-prosta-cis-5-ene-16-yneoic acid, weighing 270 mg., was collected. $^1$H- nmr (CDCl$_3$) ppm ($\delta$): 1.00 (t, 3, CH$_3$), 1.12–2.64 (m, 20), 3.95–4.50 (m, 2), 5.12–5.25 (m, 2, olefinic protons), 5.52–5.88 (bs. 3, COOH and hydroxyls). IR (CHCl$_3$)cm$^{-1}$: 1710 (COOH), 1740 (ketone).

EXAMPLE 22A

Hydrolysis of the products of Example 21A by the above procedure affords the following compounds.

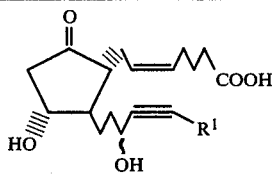

| R$^1$ | % yield |
|---|---|
| —CH$_2$(CH$_2$)$_2$CH$_3$ | 64 |
| —CH$_2$(CH$_2$)$_3$CH$_3$ | 33 |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>\|<br>CH$_3$ | — |

EXAMPLE 23

9-oxo-11α,15-dihydroxyprosta-cis-5-ene-16-yneoic acid p-biphenylyl ester (XVa, R$^1$=n-C$_3$H$_7$)

To a partial solution of 850 mg. (5 mmole) p-phenylphenol in 20 ml. anhydrous methylene chloride in a dry nitrogen atmosphere was added 170 mg. (0.5 mmole) 9-oxo-11α,15-dihydroxyprosta-cis-5-ene-16-yneoic acid (XIVa, R$^1$=n-C$_3$H$_7$) and 155 mg. (0.75 mmole) diicyclohexylcarbodiimide in 5 ml. anhydrous methylene chloride was then added dropwise over one hour. After stirring an additional 30 minutes at room temperature, the solvent was evaporated and the residue purified by column chromatography on 50 g. silica gel (Baker "Analyzed" Reagent 60–200 mesh). After elution of high R$_f$ impurities, 156 mg. of the title compound was collected, M.P. 83°–103°.

EXAMPLE 23A

Esterification of the products obtained in Example 22A by the above procedure affords the following compounds (XVa)

| R$^1$ | Yield, % | M.P. °C. |
|---|---|---|
| —CH$_2$(CH$_2$)$_2$CH$_3$ | 26 | 81–88 |
| —CH$_2$(CH$_2$)$_3$CH$_3$ | 57 | 64–84 |
| H | — | — |
| CH$_3$ | — | — |
| —CH$_2$(CH$_2$)$_4$CH(CH$_3$)$_2$ | — | — |
| —CH$_2$CH(CH$_2$)$_7$CH$_3$<br>\|<br>CH$_3$ | — | — |

EXAMPLE 24

9α,11α,15-Trihydroxy-prosta-cis-5-ene-16-yneoic acid (XVIa, R$^1$=n-C$_3$H$_7$)

A solution of 317 mg. (0.61 mmole) 9α-hydroxy-11α-(tetrahydropyran-2-yloxy)-15-(tetrahydropyran-2-yloxy)prosta-cis-5-ene-16-yneoic acid (XIIa, R$^1$=n-C$_3$H$_7$) in 15 ml. of a 65:35 mixture of glacial acetic acid/water was stirred under nitrogen at 27° overnight, then concentrated in vacuo by rotary evaporation. The resultant crude oil was purified by chromatography on 25 g. silica gel (Mallinckrodt CC-7 100–200 mesh). After elution of less polar impurities, fractions containing 160 mg. of the title compound were collected.

When the compounds obtained in Example 20A are hydrolyzed by the above procedure, the following compounds are similarly obtained.

| R$^1$ | % yield |
|---|---|
| —CH$_2$(CH$_2$)$_2$CH$_3$ | — |
| —CH$_2$(CH$_2$)$_3$CH$_3$ | 71 |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>\|<br>CH$_3$ | — |

EXAMPLE 25

2-[5α-Hydroxy-3α-(tetrahydropyran-2-yloxy)-2β-(3-hydroxy-oct-cis-4-ene-1-yl)cyclopent-1α-yl]acetic acid, γ-lactone (IXb, R$^1$=n-C$_3$H$_7$)

A solution of 1.05 g. (3.0 mmole) 2-[5α-hydroxy-3α-(tetrahydropyran-2-yloxy)-2β-(3-hydroxy-oct-4-yne-1-yl)cyclopent-1α-yl]acetic acid, γ-lactone (IXa, R$^1$=n-C$_3$H$_7$) in 15 ml. of anhydrous benzene containing 3 drops of quinoline was hydrogenated at atmospheric pressure over 45 mg. of Lindlar catalyst. After 3 hrs., the rate of hydrogen uptake stopped (67 ml. H$_2$ had been absorbed). The reaction mixture was filtered and evaporated to give 1.1 g. crude material which was purified by column chromatography on 60 g. silica gel (Baker "Analyzed" Reagent 60–200 mesh). The yield of pure title compound was 1.0 g. (95%).

EXAMPLE 25A

When the compounds obtained in Example 17A are hydrogenated over Lindlar catalyst by the above procedure, the following compounds of formula (IXb) are likewise obtained.

(IXb)

| $R^1$ | Yield, % |
|---|---|
| —CH$_2$(CH$_2$)$_2$CH$_3$ | 77 |
| —CH$_2$(CH$_2$)$_3$CH$_3$ | — |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>\|<br>CH$_3$ | — |

EXAMPLE 26

When the compounds of formula (IXb) obtained in Examples 25 and 25A are treated with 2,3-dihydropyran according to the procedure of Example 18, the following compounds of formula (Xb) are obtained.

(Xb)

| $R^1$ | Yield, % |
|---|---|
| —CH$_2$CH$_2$CH$_3$ | 100 (crude) |
| —CH$_2$(CH$_2$)$_2$CH$_3$ | 96 (crude) |
| H | — |
| CH$_3$ | — |

EXAMPLE 26A

When the compounds of formula (Xa) obtained in Example 18A are hydrogenated over Lindlar catalyst by the procedure of Example 25, the following compounds of formula (Xb) are obtained.

| $R^1$ | Yield, % |
|---|---|
| —CH$_2$(CH$_2$)$_2$CH$_3$ | — |
| —CH$_2$(CH$_2$)$_3$CH$_3$ | 87 |
| —CH$_2$(CH$_2$)$_4$CH(CH$_3$)$_2$ | — |
| —CH$_2$CH(CH$_2$)$_7$CH$_3$<br>\|<br>CH$_3$ | — |

EXAMPLE 27

2-[5α-Hydroxy-3α-(tetrahydropyran-2-yloxy)-2β-(3-{tetrahydropyran-2-yloxy}-oct-cis-4-ene-1-yl)cyclopent-1α-yl]acetaldehyde, γ-hemiacetal (XIb, $R^1$=n-C$_3$H$_7$)

A solution of 2.94 g. (6.75 mmole) 2-[5α-hydroxy-3α-(tetrahydropyran-2-yloxy)-2β-(3-{tetrahydropyran-2-yloxy}-oct-cis-4-ene-1-yl)cyclopent-1α-yl]acetic acid, γ-lactone (Xb, $R^1$=n-C$_3$H$_7$) in 50 ml. anhydrous toluene was cooled to −78° in a dry nitrogen atmosphere. To this cooled solution was added 9.25 ml. (7.4 mmole) of 20% diisobutylaluminum hydride in n-hexane (Alfa Inorganics) dropwise over a 20 minute period at such a rate that the temperature remained below −66°. After an additional 45 minutes of stirring at −78°, the reaction was diluted with ether (250 ml.). The ether solution was washed with 50% (w/w) sodium potassium tartrate solution (2×50 ml.), dried (MgSO$_4$) and concentrated to yield 3.4 g. of crude product which was purified by column chromatography on 110 g. of silica gel (Baker "Analyzed" Reagent). The yield of pure title compounds was 2.48 g.

EXAMPLE 27A

When the compounds of formula (Xb) prepared in Examples 26 and 26A are reduced with diisobutylaluminum hydride according to the above procedure, the following compounds of formula (XIb) are obtained.

(XIb)

| $R^1$ | Yield, % |
|---|---|
| —CH$_2$(CH$_2$)$_2$CH$_3$ | 74 |
| —CH$_2$(CH$_2$)$_3$CH$_3$ | 67 |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>\|<br>CH$_3$ | — |

EXAMPLE 28

9α-Hydroxy-11α-(tetrahydropyran-2-yloxy)-15-(tetrahydropyran-2-yloxy)prosta-cis-5,16-dienoic acid (XIIb, $R^1$=n-C$_3$H$_7$)

To a solution of 6.05 g. (13.7 mmole) (4-carboxy-n-butyl)triphenylphosphonium bromide in 30 ml. of anhydrous dimethylsulfoxide in a dry nitrogen atmosphere was added 14 ml. (26 mmole) of 1.85 M solution of sodium methylsulfinylmethide in dry dimethylsulfoxide. To this red ylide solution at 40° (oil bath) was added dropwise a solution of 1.9 g. (4.4 mmole) 2-[5α-hydroxy-3α-(tetrahydropyran-2-yloxy)-2β-(3-{tetrahydropyran-2-yloxy}-oct-cis-4-ene-1-yl)cyclopent-1α-yl]acetaldehyde, γ-hemiacetal (XIb, $R^1$=n-C$_3$H$_7$) in 20 ml. of dry dimethylsulfoxide over a period of 10 minutes. After 45 minutes at 40°, the reaction was poured onto ice water. The basic aqueous solution (300 ml.) was covered with ethyl acetate (300 ml.) and with vigorous stirring was acidified to pH∼3 with 1 N aqueous hydrochloric acid. The acidic solution was extracted with ethyl acetate (2×150 ml.) and the combined organic extracts washed with saturated brine, dried (Na$_2$SO$_4$) and evaporated to a solid residue which was triturated with ether and filtered. The filtrate was concentrated and by column chromatography on 250 g. silica gel (Baker "Analyzed" Reagent 60–200 mesh). After removal of high R$_f$ impurities, 2.82 g. of purified title compound was collected.

EXAMPLE 28A

When the compounds of formula (XIb) prepared in Example 27A are used as starting material in the above procedure in place of 2-[5α-hydroxy-3α-(tetrahydropyran-2-yloxy)-2β-(3-{tetrahydropyran-2-yloxy}-oct-cis-4-ene-1-yl)cyclopent-1α-yl]acetaldehyde, γ-hemiacetal, the following compounds of formula (XIIb) are prepared.

(XIIb)

| $R^1$ | Yield, % |
|---|---|
| —CH$_2$(CH$_2$)$_2$CH$_3$ | 83 |
| —CH$_2$(CH$_2$)$_3$CH$_3$ | 95 |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>       \|<br>      CH$_3$ | — |

EXAMPLE 29

9-oxo-11α-(tetrahydropyran-2-yloxy)-15-(tetrahydropyran-2-yloxy)-prosta-cis-5,16-dienoic acid (XIIIb, $R^1$=n-C$_3$H$_7$)

To a solution of 1.4 g. (2.8 mmole) 9α-hydroxy-11α-(tetrahydropyran-2-yloxy)-15-(tetrahydropyran-2-yloxy)prosta-cis-5,16-dienoic acid (XIIb, $R^1$=n-C$_3$H$_7$) in 100 ml. of acetone at −10° in a dry nitrogen atmosphere was added 1.2 ml. (3.0 mmole) of 2.67 M Jones' reagent. After 10 minutes at −10°, the reaction was poured onto ethyl acetate (150 ml.), washed with water (50 ml.), dried (Na$_2$SO$_4$) and concentrated to yield 1.6 g. crude title compound.

EXAMPLE 29A

When the compounds of formula (XIIb) obtained in Example 28A are treated with Jones' reagent in the above procedure, the following compounds of formula (XIIIb) are similarly obtained.

(XIIIb)

| $R^1$ | Yield, % |
|---|---|
| —CH$_2$(CH$_2$)$_2$CH$_3$ | 100 (crude) |
| —CH$_2$(CH$_2$)$_3$CH$_3$ | 100 (crude) |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>       \|<br>      CH$_3$ | — |

EXAMPLE 30

9-oxo-11α,15-dihydroxy-prosta-cis-5,16-dienoic acid (XIVb, $R^1$=n-C$_3$H$_7$)

A solution of 1.6 g. of 9-oxo-11α-(tetrahydropyran-2-yloxy)-15-(tetrahydropyran-2-yloxy)prosta-cis-5,16-dienoic acid (XIIIb, $R^1$=n-C$_3$H$_7$) in a 65:35 mixture of glacial acetic acid/water was stirred under nitrogen at 27° overnight, then concentrated by rotary evaporation. The resultant crude oil was purified by chromatography on 100 g. silica gel (Mallinckrodt CC-7 100–200 mesh). After elution of less polar impurities, the fractions containing the title compound were collected and evaporated to dryness to obtain 270 mg. (25%).

EXAMPLE 30A

When the compounds of formula (XIIIb) obtained in Example 29A are hydrolyzed by the above procedure, the following compounds are obtained.

(XIVb)

| $R^1$ | Yield, % |
|---|---|
| —CH$_2$(CH$_2$)$_2$CH$_3$ | 27 |
| —CH$_2$(CH$_2$)$_3$CH$_3$ | 25 |
| H | — |
| CH$_3$ | — |
| —CH$_2$(CH$_2$)$_4$CH(CH$_3$)$_2$ | — |
| —CH$_2$CH(CH$_2$)$_7$CH$_3$<br>       \|<br>      CH$_3$ | — |

EXAMPLE 31

When the compounds of formula (XIIb) obtained in Examples 28 and 28A are hydrolyzed by the procedure of Example 30, the following compounds are obtained.

(XVIb)

| $R^1$ | Yield, % |
|---|---|
| —CH$_2$CH$_2$CH$_3$ | 54 |
| —CH$_2$(CH$_2$)$_2$CH$_3$ | 63 |
| —CH$_2$(CH$_2$)$_3$CH$_3$ | 54 |
| —H | — |
| —CH$_3$ | — |
| —CH$_2$(CH$_2$)$_4$CH(CH$_3$)$_2$ | — |
| —CH$_2$CH(CH$_2$)$_7$CH$_3$<br>       \|<br>      CH$_3$ | — |

EXAMPLE 32

By esterification of the compounds prepared in Examples 30 and 30A with p-phenylphenol by the procedure described in Example 16, the following compounds are obtained.

| $R^1$ | M.P. °C. | Yield, % |
|---|---|---|
| —CH$_2$CH$_2$CH$_3$ | 88–110 | 13 |
| —CH$_2$(CH$_2$)$_2$CH$_3$ | 88–93 | 65 |
| —CH$_2$(CH$_2$)$_3$CH$_3$ | 64–84 | 56 |
| —H | — | — |
| —CH$_3$ | — | — |
| —CH$_2$(CH$_2$)$_4$CH(CH$_3$)$_2$ | — | — |
| —CH$_2$CH(CH$_2$)$_7$CH$_3$<br>$\quad\quad\quad$ \|<br>$\quad\quad\quad$ CH$_3$ | — | — |

EXAMPLE 33

2-[5α-Hydroxy-3α-(tetrahydropyran-2-yloxy)-2β-(3-hydroxypent-4-ene-1-yl)cyclopent-1α-yl]acetic acid, γ-lactone (IX, R$^1$=H)

To a solution of 1.97 g. (7 mmole) 2-[5α-hydroxy-3α-(tetrahydropyran-2-yloxy)-2β-(2-formylethyl)cyclopent-1α-yl]acetic acid, γ-lactone (VIII) in 40 ml. of anhydrous tetrahydropyran at −78° in a dry nitrogen atmosphere was added dropwise 6.3 ml. (14 mmole) 1.97 M vinyl lithium (Alfa Inorganics) in n-pentane. The reaction was stirred at −78° C. for 20 minutes, then poured onto 200 ml. of ether/ethyl acetate (50/50) containing ice-water. The organic layer was separated, washed with brine, dried (Na$_2$SO$_4$) and evaporated to give 3 g. crude product, which was purified by column chromatography on 150 g. of silica gel (Baker "Analyzed" Reagent 60–200 mesh). After elution of high R$_f$ impurities, 840 mg. of pure title compound was collected.

EXAMPLE 34

1-Iodo-trans-1-hexene

To a solution of 8.2 g. (0.10 mole) of 1-hexyne in 20 ml. of heptane, under a nitrogen atmosphere, was added 125 ml. (0.10 mole) of 0.8 M diisobutylaluminum hydride in n-hexane, in four portions while maintaining the temperature below 40° with a water bath. When the initial exothermic reaction had subsided, the reaction mixture was warmed at 50° for two hours. The heptane and hexane were removed in vacuo and the residue was diluted with 40 ml. of tetrahydrofuran. The resulting solution was cooled to −50° and a solution of 25.4 g. (0.10 mole) of iodine in 40 ml. of tetrahydrofuran was added. The reaction mixture was allowed to warm to room temperature. While maintaining the reaction mixture at 20°–30° (ice-bath), 20% sulfuric acid was added to decompose the diisobutylaluminum. When the isobutane evolution had diminished, the reaction mixture was poured onto a mixture of ice-20% sulfuric acid. The product was extracted with hexane and the combined extracts washed with sodium thiosulfate solution, then with saturated sodium bicarbonate solution and dried over anhydrous sodium sulfate. Distillation afforded 14.7 g. (70%) of the desired product, b.p. 60°–62° at 6 mm. The structure was verified by $^1$H-NMR.

By use of the appropriate 1-alkyne in place of 1-hexyne and following the above procedure, the following 1-iodo-trans-1-alkenes are similarly obtained:

1-Iodo-trans-1-propylene
1-Iodo-trans-1-decene
1-Iodo-trans-1-tridecene

EXAMPLE 35

2-[5α-Hydroxy-3α-(tetrahydropyran-2-yloxy)-2β-(3-hydroxy-non-trans-4-ene-1-yl)cyclopent-1α-yl]acetic acid, γ-lactone (IXc, R$^1$=n-C$_4$H$_9$)

To a solution of 282 mg. (1 mmole) 2-[5α-hydroxy-3α-(tetrahydropyran-2-yloxy)-2β-(2-formylethyl)cyclopent-1α-yl]acetic acid, γ-lactone (VIII) in 5 ml. of anhydrous tetrahydropyran at −78° for 20 minutes then added dropwise 3.5 ml. (1.9 mmole) 0.55 M trans-1-hexenyl lithium* in tetrahydrofuran/pentane. The reaction was stirred at −78° for 20 minutes then poured onto 100 ml. of ether/ethyl acetate (50/50) containing ice-water. The organic layer was separated, washed with brine, dried (Na$_2$SO$_4$) and evaporated to give 300 mg. crude product, which was purified by column chromatography on 15 g. of silica gel (Baker "Analyzed" Reagent 60–200 mesh). After elution of high R$_f$ impurities, 110 mg. of pure title compound was collected.

*trans-1-hexenyl lithium was prepared as follows:

A solution of 10.5 g. (0.05 mole) of 1-iodo-trans-1-hexane in 50 ml. of dry tetrahydrofuran was cooled to −78° under nitrogen. To this was added slowly in four portions 103 ml. (0.10 mole) of 0.97 M t-butyl lithium in pentane (lithium iodide precipitate forms) to give a pale yellow solution which was found to be 0.55 M upon titration.

EXAMPLE 35A

When the above procedure is repeated, but with the appropriate 1-iodo-trans-alkene selected from those prepared in Example 34 employed in place of the 1-iodo-trans-1-hexene used therein, the following compounds of formula (IXc) are similarly obtained.

$R^1$
—CH$_3$
—CH$_2$(CH$_2$)$_6$CH$_3$
—CH$_2$(CH$_2$)$_9$CH$_3$

EXAMPLE 36

When the compounds of formula (IXc) obtained in Examples 33, 35 and 35A are reacted with 2,3-dihydropyran by the procedure of Example 18, the following compounds of formula (Xc) are obtained.

(Xc)

| R¹ | Yield, % |
|---|---|
| —H | 100 (crude) |
| —CH₃ | — |
| —CH₂(CH₂)₂CH₃ | 87 (crude) |
| —CH₂(CH₂)₆CH₃ | — |
| —CH₂(CH₂)₉CH₃ | — |

EXAMPLE 37

When the compounds obtained in Example 36 are reduced with diisobutylaluminum hydride by the procedure of Example 19 the following compounds of formula (XIc) are produced.

(XIc)

| R¹ | Yield, % |
|---|---|
| —H | 54 |
| —CH₃ | — |
| —CH₂(CH₂)₂CH₃ | 65 |
| —CH₂(CH₂)₆CH₃ | — |
| —CH₂(CH₂)₉CH₃ | — |

EXAMPLE 38

When the products obtained in Example 37 are reacted with (4-carboxy-n-butyl)triphenylphosphonium bromide and sodium methylsulfinylmethide by the procedure described in Example 20 the following compounds of formula (XIIc) are prepared.

(XIIc)

| R¹ | Yield, % |
|---|---|
| —H | 62 |
| —CH₃ | — |
| —CH₂(CH₂)₂CH₃ | 84 |
| —CH₂(CH₂)₆CH₃ | — |
| —CH₂(CH₂)₉CH₃ | — |

EXAMPLE 39

When the products of Example 38 are oxidized by Jones' reagent according to the procedure of Example 21 the following compounds of formula (XIIIc) are obtained.

(XIIIc)

| R¹ | Yield, % |
|---|---|
| —H | 100+ (crude) |
| —CH₃ | — |
| —CH₂(CH₂)₂CH₃ | 96 (crude) |
| —CH₂(CH₂)₆CH₃ | — |
| —CH₂(CH₂)₉CH₃ | — |

EXAMPLE 40

The compounds prepared in Example 39 are hydrolyzed in acetic acid/water according to the procedure described in Example 22 to obtain the following compounds of formula (XIVc).

(XIVc)

| R¹ | Yield, % |
|---|---|
| —H | 19 |
| —CH₃ | — |
| —CH₂(CH₂)₂CH₃ | 54 |
| —CH₂(CH₂)₆CH₃ | — |
| —CH₂(CH₂)₉CH₃ | — |

EXAMPLE 41

When the compounds obtained in Example 38 are hydrolyzed in acetic acid/water according to the procedure described in Example 22, the following compounds of formula (XVIc) are obtained.

(XVIc)

| R¹ |
|---|
| —H |
| —CH₃ |
| —CH₂(CH₂)₂CH₃ |
| —CH₂(CH₂)₉CH₃ |

EXAMPLE 42

When the compounds obtained in Examples 40 and 41 are esterified with p-phenylphenol by the procedure described in Example 23, the following products are obtained.

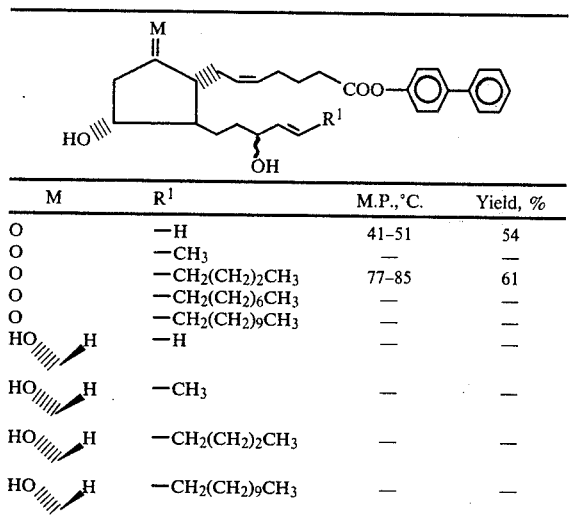

| M | R¹ | M.P., °C. | Yield, % |
|---|---|---|---|
| O | —H | 41–51 | 54 |
| O | —CH₃ | — | — |
| O | —CH₂(CH₂)₂CH₃ | 77–85 | 61 |
| O | —CH₂(CH₂)₆CH₃ | — | — |
| O | —CH₂(CH₂)₉CH₃ | — | — |
| HO⫽H | —H | — | — |
| HO⫽H | —CH₃ | — | — |
| HO⫽H | —CH₂(CH₂)₂CH₃ | — | — |
| HO⫽H | —CH₂(CH₂)₉CH₃ | — | — |

EXAMPLE 43

9-Oxo-11α,15α-dihydroxy-ω-homo-prosta-cis-5-ene-16-yneoic acid, p-biphenylyl ester and 9-oxo-11α-15β-dihydroxy-ω-homo-prosta-cis-5-ene-16-yneoic acid, p-biphenyl ester The 15-hydroxy epimers were separated by preparative thin layer chromatography as follows: On a two millimeter thick Brinkman silica gel plate was streaked an ethereal solution containing 60 mg. of 9-oxo-11α,15-dihydroxy-ω-homo-prosta-cis-5-ene-16-yneoic acid, p-biphenylyl ester (mixture of 15-HO epimers). The plate was eluted with ether to separate the epimers. The separate zones of silica gel were removed from the plate and extracted with ether and the solvent evaporated. The zone containing the slower moving epimer afforded 40 mg. of 15α-epimer, M.P. 90°–92°. The faster moving zone afforded 15 mg. of 15β-epimer, M.P. 64°–66° C.

When the above procedure is employed with each of the products prepared in Example 16, 16A, 23, 23A and 42 the separation of the 15α- and 15β-epimers is achieved in each case.

EXAMPLE 44

9,15-Dioxo-11α-hydroxyprosta-cis-5-ene-16-yneoic Acid

To a suspension of 1.20 g. of powdered active manganese dioxide [Stork and Tomasy, *Jour. Am. Chem. Soc.*, 86, 471 (1964)] in 15 ml. of dry methylene chloride is added 80 mg. of 9-oxo-11α,15-dihydroxyprosta-cis-5-ene-16-yneoic acid in portions over 15 minutes. The reaction mixture is stirred for 6 hours at room temperature, then filtered through a layer of anhydrous magnesium sulfate placed on filter paper. After washing the filter cake with methylene chloride, the filtrate and washings were combined and evaporated to dryness. The crude product was then purified by silica gel column chromatography.

When the above procedure is employed with other compounds of formulae XIV or XVI, prepared in Examples 8, 9, 30, 31, 41, and 44, the following 15-keto compounds are similarly obtained.

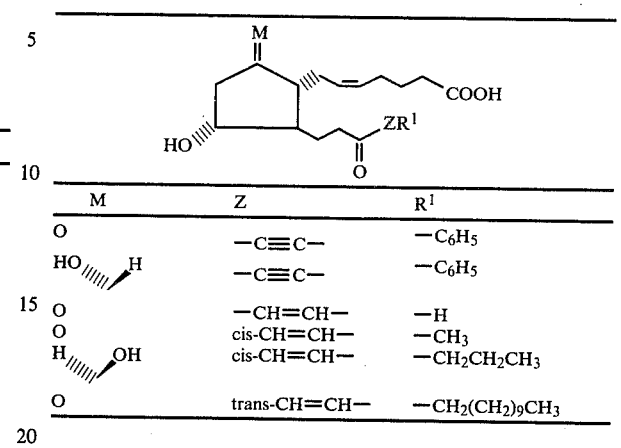

| M | Z | R¹ |
|---|---|---|
| O | —C≡C— | —C₆H₅ |
| HO⫽H | —C≡C— | —C₆H₅ |
| O | —CH=CH— | —H |
| O | cis-CH=CH— | —CH₃ |
| H⫽OH | cis-CH=CH— | —CH₂CH₂CH₃ |
| O | trans-CH=CH— | —CH₂(CH₂)₉CH₃ |

What is claimed is:

1. A compound of the formula

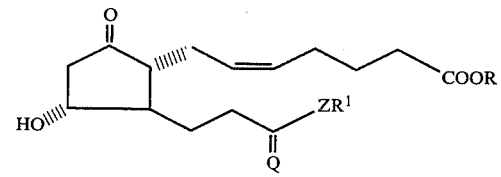

wherein

R is hydrogen or biphenylyl;

R¹ is a member selected from the group consisting of hydrogen and alkyl having from one to eleven carbon atoms;

Q is a member selected from the group consisting of oxygen,

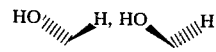

and mixtures of

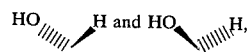

and Z is -C≡C-.

2. A compound according to claim 1 wherein Q is said mixture of

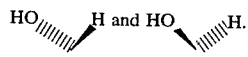

3. A method of inducing bronchodilation in a mammal which comprises administering to said mammal a bronchodilating amount of a compound of claim 1.

4. A method of inducing bronchodilation in a mammal which comprises administering to said mammal a bronchodilating amount of a compound of claim 2.

5. A bronchodilating composition comprising a bronchodilating amount of a compound of claim 1 and a pharmaceutically acceptable carrier.

* * * * *